US005786482A

United States Patent [19]
Bringmann et al.

[11] Patent Number: 5,786,482
[45] Date of Patent: Jul. 28, 1998

[54] DIMERIC ARYLISOQUINOLINE ALKALOIDS AND SYNTHESIS METHOD THEREOF

[75] Inventors: Gerhard Bringmann, Würzburg, Germany; Michael R. Boyd, Ijamsville, Md.; Roland Götz, Rothenburg, Germany; T. Ross Kelly, Watertown, Mass.

[73] Assignees: The United States of America as represented by the Department of Health and Human Services, Washington, D.C.; The Trustees of Boston College, Chestnut Hill, Mass.

[21] Appl. No.: 721,084

[22] Filed: Sep. 24, 1996

Related U.S. Application Data

[62] Division of Ser. No. 363,684, Dec. 23, 1994, Pat. No. 5,578,729, which is a continuation of Ser. No. 305,211, Sep. 13, 1994, abandoned, which is a continuation-in-part of Ser. No. 279,291, Jul. 22, 1994, Pat. No. 5,552,550, and Ser. No. 279,339, Jul. 22, 1994, Pat. No. 5,571,919.

[51] Int. Cl.$^6$ .................................................. C07D 401/10
[52] U.S. Cl. ........................... 546/140; 546/146; 546/147
[58] Field of Search .................................. 546/139, 140, 546/146, 147

[56] References Cited

U.S. PATENT DOCUMENTS

| | | | |
|---|---|---|---|
| 3,751,419 | 8/1973 | Ziegler | 546/146 |
| 4,096,190 | 6/1978 | Rutledge | 514/307 |
| 5,260,315 | 11/1993 | Bringmann et al. | 514/307 |
| 5,409,938 | 4/1995 | Boyd et al. | 514/307 |
| 5,455,251 | 10/1995 | Boyd et al. | 514/308 |
| 5,552,550 | 9/1996 | Bringmann et al. | 546/146 |
| 5,571,919 | 11/1996 | Bringmann et al. | 546/140 |
| 5,578,729 | 11/1996 | Bringmann et al. | 546/140 |
| 5,639,761 | 6/1997 | Francois et al. | 546/140 |
| 5,654,432 | 8/1997 | Boyd et al. | 546/140 |

FOREIGN PATENT DOCUMENTS

WO 92/18125  10/1992  WIPO.
WO 94/24108  10/1994  WIPO.

OTHER PUBLICATIONS

Bringmann, "The Naphthyl Isoquinoline Alkaloids," in *The Alkaloids*, vol. 29, Brossi, ed., Academic Press, New York 141–184 (1986).
Gustafson et al., "AIDS–Antiviral Sulfolipids from Cyanobacteria (Blue–Green Algae)," *J. National Cancer Institute*, 81(16) (Aug. 16, 1989).
Ruangrungsi et al., "Traditional Medicinal Plants of Thailand. V. Ancistrotectorine, A New Naphthalene–Isoquinoline Alkaloid from *Ancistrocladus tectorius*, " *J. Natural Products*, 48(4), 529–535 (Jul.–Aug. 1985).
Sandström et al., "Antiviral Therapy in AIDS Clinical Pharmacological Properties and Therapeutic Experience To Date," *Drugs*, 34, 373–390 (1987).
Snieckus, "Directed Ortho Metalation. Tertiary Amide and O–Carbamate Directors in Synthetic Strategies for Polysubstituted Aromatics," *Chemical Reviews*, 90, 879–933 (1990).
Stuart–Harris et al., in *The Background to Chemotherapy of Virus Diseases to Chemotherapy of Virus Diseases*, Chapter 5, 76–77 (Charles C. Thomas Publishers, Springfield, IL, 1965).
Weislow et al., "New Soluble–Formazan Assay for HIV–1 Cytopathic Effects: Application to High–Flux Screening of Synthetic and Natural Products for AIDS–Antiviral Activity," *J. National Cancer Institute*, 81(8), 577–586 (Apr. 19, 1989).
Anonymous, "Natural Product Agents in Development by the United States National Cancer Institute (NCI)," *J. Natural Products*, 55(7), 1018–1019 (1992).
Baptistella et al., "1, 8–Diazabicyclo[5.4.0]undec–7–ene as a Mild Deprotective Agent for Acetyl Groups," *Synthesis*, 436–438 (1989).
Benfield et al., "Studies of Fungal and Plant Laccases," *Phytochemistry*, 3, 79–88 (1964).
Berthelot et al., "Bromation Regioselective en Serie Aromatique. I: Monobromation en Position para de Phenols et d' amines Aromatiques par le Tribromure de Tetrabutylammonium," *Can.J. Chem.*, 67, 2061–2066 (1989).
Bobbitt, et al., "Electrochemistry of Natural Products. III. A Stereoselective, Stereospecific Phenol Coupling Reaction," *J. Am. Chem. Soc.*, 93, 3551–3552 (1971).
Boyd et al., "Novel Alkaloids from the Tropical Plant *Ancistrocladus Abbreviatis* Inhibit Cell Killing by HIV–1 and HIV–2," *J. Medicinal Chemistry*, 34(12), 3402–3405 (1991).
Boyd et al., *Chemical Abstracts*, 117(11), Abstract No. 104,239k, p. 98, Sep. 14, 1992.
Boyd et al., "Anti–HIV Michellamines from *Ancistrocladus korupensis*," *J. Medicinal Chemistry*, 37(12), 1740–1745 (1994).
Bringmann et al., "Circular Dichroism of Michellamines: Independent Assignment of Axial Chirality by Calculated and Experimental CD Spectra," *Tetrahedron*, 50(26), 7807–7814 (1994).
Bringmann et al., "First Total Synthesis of Korupensamines A and B," *Heterocycles*, 39(2), 503–508 (1994).

(List continued on next page.)

*Primary Examiner*—Zinna Northington Davis
*Attorney, Agent, or Firm*—Leydig, Voit & Mayer, Ltd.

[57] ABSTRACT

The present invention provides a method of preparing dimeric arylisoquinoline alkaloids by coupling two isoquinoline building blocks, which may be the same or different, together with a symmetrical or nonsymmetrical biaryl building block to form homodimers or heterodimers, including the antiviral michellamines. The present invention also provides new, medically useful homodimeric and heterodimeric arylisoquinoline compounds and derivatives thereof.

18 Claims, 21 Drawing Sheets

OTHER PUBLICATIONS

Bringmann et al., "Biomimetic Oxidative Dimerization of Korupensamine A: Completion of the First Total Synthesis of Michellamines A, B, and C," *Tetrahedron*, 50(32), 9643–9648 (1994).

Bringmann et al., *Tetrahedron*, vol. 50, No. 26, Jun. 1994, pp. 7807–7814.

Bringmann et al., "The Synthesis of All Possible Isometric 6, 8–Dioxygenated 1, 3–Dimethyl–1, 2, 3, 4–tetrahydroisoquinoline Methyl Ethers—Useful Chiral Building Blocks for Naphthylisoquinoline Alkaloids," *Liebigs Ann. Chem.*, 877–878 (1993).

Bringmann et al., "The Absolute Configuration of Michellamine B, A 'Dimetric,' Anti–HIV–Active Naphthylisoquinoline Alkaloid," *Angew. Chem. Int. Ed. Engl.*, 32(8), 1190–1191 (1993).

Bringmann et al., "A New Atropisometric Dioncophylline A Derivative from *Triphyophyllum peltatum*," *Planta Med.*, 59 (Suppl.), A621–622 (1993).

Bringmann et al., "The Cultivation of Tropical Lianas of the Genus Ancistrocladus," *Planta Med.*, 59 (Suppl.), A623–624 (1993).

Bringmann et al., "Ancistrobrevine B, The First Naphthylisoquinoline Alkaloid with a 5,8'–Coupling Site, and Related Compounds from *Ancistrocladus abbreviatus*," *Phytochemistry*, 31(11), 4011–4014 (1992).

Bringmann et al., "(+)–Dioncophyllacine A, A Naphthylisoquinoline Alkaloid with a 4–Methoxy Substituent from the Leaves of *Triphyophyllum peltatum*," *Phytochemistry*, 31(11), 4015–4108 (1992).

Bringmann et al., "Dioncophylline C from the Roots of *Triphtophtllum peltatum*, the First 5,1' –Coupled Dioncophyllaceae Alkaloid," *Phytochemistry*, 31(11), 4019–4024 (1992).

Bringmann et al., "Ancistrobrevine D: An unusual Alkaloid from *Ancistrocladus abbreviatus*," *Planta Med.*, 58 (Suppl. 1), A703–704 (1992).

Bringmann et al., "Stereocontrolled Ring Opening of *Axially Prostereogenic* Biaryl Lactones with Hydrogen Nucleophiles: Directed Synthesis of a Dioncophylline A Precursor and (Optionally) its Atroodiastereomer," *Synthesis*, 825–827 (1991).

Bringmann et al., "Astrop–diastereomer Separation by Racemate Resolution Techniques: N–Methyl–Dioncophylline A and its 7–Epimer from *Ancistrocladus abbreviatus*," *Phytochemistry*, 30(4), 1307–1310 (1991).

Bringmann et al., "Dioncopeltine A and Dioncolactone A: Alkaloids from *Triphyophyllum peltatum*," *Phtochemistry*, 30(5), 1691–1696 (1991).

Bringmann et al., "Dioncophylline B, A Naphthylisoquinoline Alkaloid with a New Coupling Type from *Triphyophyllum peltatum*," *Phytochemistry*, 30(11), 3845–3847 (1991).

Bringmann et al., "On the Biosynthesis of Acetogenic Tetrahydroisoquinoline Alkaloids: First In Vivo Feeding Experiments," *Planta Med.*, 57 (Suppl. 2), A98 (1991).

Bringmann et al., "On the Structure of the Dioncophyllacea Alkaloids Dioncophylline A (Triphyophylline) and 'O–Methyl–Triphyophylline,'" *Tetrahedron Letters*, 31(5), 639–642 (1990).

Bringmann et al., "The First Total Synthesis of (–)–Dioncophylline A ('Triphyophylline') and of Seleted Stereoisomers: Complete (Revised) Stereostructure," *Tetrahedron Letters*, 31(5), 643–646 (1990).

Bringmann et al., "Chiral Economy with Respect to Rotational Isomerism: Rationalism Synthesis of Hamatine and (Optionally) Ancistroladine from Joint Helical Precursors," *Heterocycles*, 28(1), 137–142 (1989).

Bringmann et al., "Atropdiastereoselective Ring Opening of Bridged, 'Axial–prostereogenic' Biaryls: Directed Synthesis of (+)–Ancistrocladisine," *Angew. Chem. Int. Ed. Engl.*, 28(12), 1672–1673 (1989).

Bringmann, *The Alkaloids*, 29 (Brossi, ed.), Academic Press, New York, 1986, pp. 141–184.

Bringmann et al., "Regioselective and Atropoisomeric–Selective Aryl Coupling to give Naphthyl Isoquinoline Alkaloids: The First Total Synthesis of (–)–Ancistrocladine," *Angew. Chem. Int. Ed. Engl.*, 25(10), 913–915 (1986).

Bringmann et al., "Biomimetische Synthesen beider Molekulhalften der Ancistrocladus–und der Triphyophyllum–Alkaloide aus gemeinsamen Vorstufen," *Liebigs Ann. Chem.*, 2126–2134 (1985).

Bringmann et al., "Isoquinolines and Naphthalines from $\beta$–Polyketones: Model Reactions for an Extraordinary Alkaloid Biosynthesis," *Angew. Chem. Int. Ed. Engl.*, 21(3), 200–201 (1982).

Bringmann et al., "Improved Methods for Dehydration and Hydroxy/Halogen Exchange Using Novel Combinations of Triphenylphosphine and Halogenated Ethanes," *Synthesis*, 139–141 (1983).

Casey et al., "Interconversion of $\gamma$–Silyl $\alpha$, $\beta$–Unsaturated Carbonyl Compounds and Siloxybutadienes by 1, 5–Shifts of Silicon Between Carbon and Oxygen," *J. Org. Chem.*, 46, 2089–2092 (1981).

Chapman et al., "Synthesis of Triflates of 2, 4–Dinitrophenol and N–Hydroxysuccinimide," *Synthesis*, 591–592 (1971).

Farina et al., "Polycyclic Hydroxyguinones—VIII," *Tetrahedron*, 38(10), 1531–1537 (1982).

Flaig et al., "Reaktionen Mit Oxodierenden Enzymen Aus Mikroorganismen," *Planta Med.*, 9, 123–139 (1961).

Fleischhauer et al., "Messung und Berechnung der CD–Spektren der Biaryl–Alkaloids Ancistrocladein und Dioncophyllein A," *Z. Naturforsch*, 48b, 140–148 (1993).

Francois et al., "Activity of Extracts and Naphthylisoquinoline Alkaloids from *Triphyophyllum peltatum*, *Ancistrocladus abbreviatus* and *A. barteri* against *Plasmodium falciparum* In Vitro," *Phytochemistry*, 35(6), 1461–1464 (1994).

Gulakowski et al., "A Semiautomatic Multiparameter Approach for Anti–HIV Drug Screening," *J. Virological Methods*, 33, 87–100 (1991).

Handford et al., "Synthesis of Eleutherolic Acid," *J. Chem. Soc.*, 3896–3897 (1963).

Harel et al., "Purification and Multiplicity of Catechol Oxidase from Apple Chloroplasts," *Phytochemistry*, 4, 783–790 (1965).

Hodgson et al., "The Action of Fuming Nitric Acid on the 4–Halogeno–2: 6–dibromo–phenols and –anisoles. Anomalous Behaviour of Fluorine Derivatives," *J. Chem. Soc.*, 1085–1087 (1930).

Holland, in *Organic Synthesis with Oxidative Enzymes*, Chapter 8, Miscellaneous Oxidative Bioconversions, "1. Oxidative Coupling of Phenols and the Formation of Quinones," VCH, Weinheim, 341–351, 380–381 (1992).

Hoye et al., "Total Synthesis of Michellamines A–C:Important Anti–HIV Agents," *Tetrahedron Letters*, 35(47), 8747–8750 (1994).

Ismail et al., "Synthesis of Benzothiazoles. $\alpha$–Amino–(4–hydroxy–6–benzothiazolyl) Propionic Acid," *J. Org. Chem.*, 45, 2243–2246 (1980).

Kelly et al., "Convergent total Synthesis of the Michellamines," *Tetrahedron Letters*, 35(41), 7621–7624 (1994).

Laatsch, "Isodiospyrin und Elliptinon.—Sythese 6,6'–dimerer Bijuglone durch Phenoloxidation," *Liebigs Ann. Chem.*, 319–339 (1984).

Laatsch, "Synthese von Biramentaceon, Mamegakinon und Rotundichinon," *Liebigs Ann. Chem.*, 1321–1347 (1980).

Lipshutz et al., "Cyanocuprate–Mediated Intramolecular Biaryl Couplings Applied to an Ellagitannin. Synthesis of (+)–O–Permethyltellimagrandin II," *Tetrahedron*, 35(31), 5567–5570 (1994).

Manfredi et al., "Novel Alkaloids from the Tropical Plant *Ancistrocladus abbreviatus* Inhibit Cell Killing by HIV–1 and HIV–2," *Journal of Medicinal Chemistry*, 34(12), 3402–3405 (1991).

McMahon et al., "Diarylsulfones, a New Class of Nonnucleoside Antiviral Inhibitors of Human Immunodeficiency Virus Type I Reverse Transcriptase," *Antimicrobial Agents and Chemotherapy*, 37(4), 754–760 (1993).

Nicholl, in *An Introduction to Genetic Engineering*, Cambridge Univ. Press, Cambridge, pp. 1–5 & 127–130 (1994).

Old et al., in *Principles of Gene Manipulation*, Blackwell Scientific Publishers, London, pp. 3–13 & 108–221 (1992).

Owton et al., "tert–Butyl–3–Carboxyethyl–3–Phosphonodiethylpropionate. A Novel Reagent for Stobbe–like Condensations," *Synthetic Communications*, 23(15), 2119–2125 (1993).

Pearson et al., "The Ortho Bromination of Phenols," *J. Org. Chem.*, 32, 2358–2360 (1967).

Rizzacasa et al., "Synthetic Approaches to the Alkaloids of the Ancistrocladaceae: Dehydroancistrocladisinie," *J. Chem. Soc.*, 301–302 (1989).

Rizzcasa et al., "The Synthesis of Stypandrol, A Toxic Binaphthalenetetrol Isolated from *Stypandra imbricata*: New Synthesis of Dianellidin and Stypandrone," *Aust. J. Chem.*, 41, 1087–1097 (1988).

Robb et al., On the Heterogeneity of the Tyrosinase of Broad Bean (Vicia Faba L.), *Phytochemistry*, 4, 731–740 (1965).

Saunders, *Peroxidase*, Butterworth, London, pp. 1–52 (1964).

Savard et al., "Reactions of Ketene Acetals—14," *Tetrahedron*, 40(18), 3455–3464 (1984).

Scott, "Oxidative Coupling of Phenolic Compounds," in *Quarterly Reviews*, (London), 19, 1–35 (1965).

Shimizu et al., "A Simple and Efficient Synthesis of 2–, 3–, or 4–(2–Nitrophenyl) pyridine Derivatives via Palladium Catalyzed Ullmann Cross–Coupling Reaction," *Tetrahedron Letters*, 34(21), 3421–3424 (1993).

Sofer, *Introduction to Genetic Engineering*, Butterworth–Heinemann, Stoneham, MA, pp. 1–21 & 103–126 (1991).

Steinberg et al., in *Recombinant DNA Technology Concepts and Biomedical Applications*, Prentice Hall, Englewood Cliffs, NJ, pp. 81–124 & 150–162 (1993).

Supko et al., "Determination of Michellamine B in Biological Fluids by High–Performance Liquid Chromatograph with Fluorescence Detection," *Analytical Biochemistry*, 216, 52–60 (1994).

Suzuki, "New Synthetic Transformations via Organoboron Compounds," *Pur & Appl. Chem.*, 66(2), 213–222 (1994).

Thomas et al., "*Ancistrocladus korupensis* (Ancistrocladaceae): A New Specis of Liana from Cameroon," *Novon*, 3(4), 494–498 (1993).

Vilietstra et al., "Trimethylacetic Formic Anhydride. Improved Preparation and Use As a Highly Efficient and Selective N–formylating Reagent," *J. Royal Netherlands Chemical Society*, 101, 460–462 (1982).

Atanabe et al., "Synthesis of Sterically Hindered Biaryls via the Palladium–Catalyzed Cross–Coupling Reaction of Arylboronic Acids or their Esters with Haloarenes," *Synlett*, 207–210 (Mar. 1992).

Whiting, in *Comprehensive Organic Synthesis*, (Trost and Fleming, eds.), Peragamon Press, Oxford, pp. 659–703 (1991).

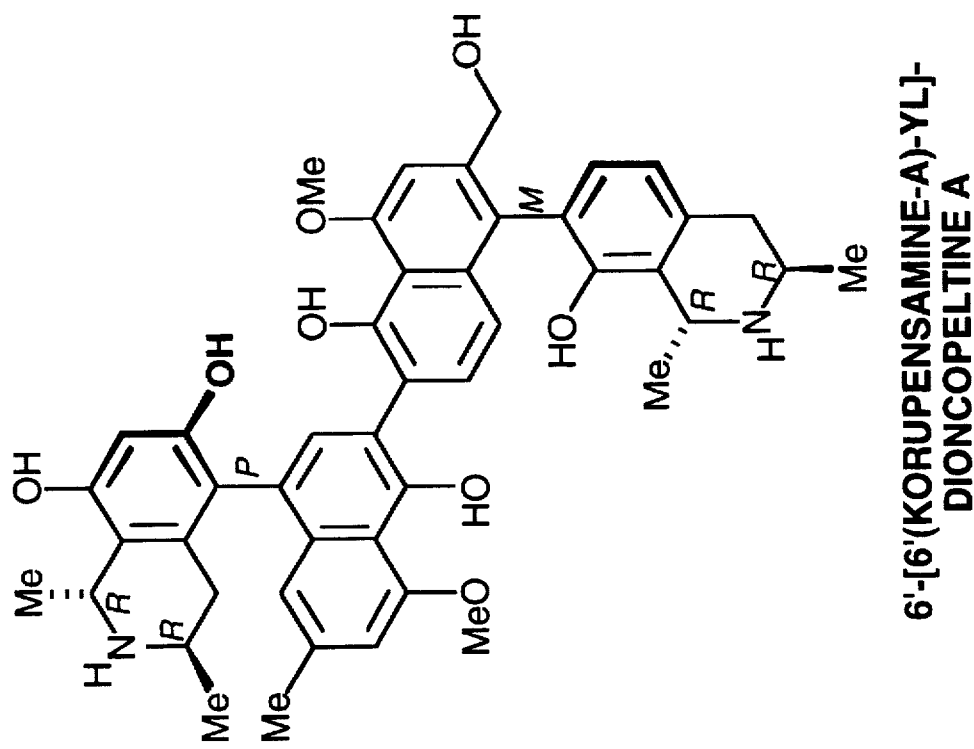
FIG. 9E
6'-[6'(KORUPENSAMINE-A)-YL]-DIONCOPELTINE A
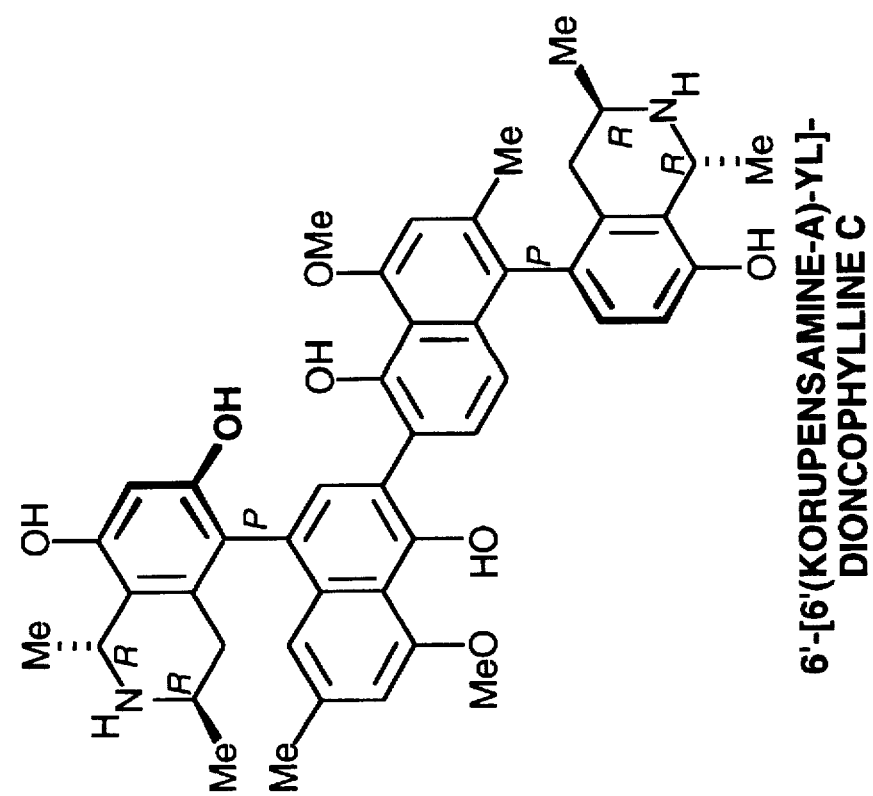
6'-[6'(KORUPENSAMINE-A)-YL]-DIONCOPHYLLINE C

6'-[6'(KORUPENSAMINE-B)-YL]-DIONCOPELTINE A

6'-[6'(KORUPENSAMINE-B)-YL]-DIONCOPHYLLINE C

DIMERIC ARYLISOQUINOLINE ALKALOIDS AND SYNTHESIS METHOD THEREOF

CROSS-REFERENCE TO RELATED APPLICATIONS

This patent application is a divisional of U.S patent application Ser. No. 08/363,684, filed Dec. 23, 1994, now U.S. Pat. No. 5,578,729 which is a continuation of U.S. patent application Ser. No. 08/305,211, filed Sep. 13, 1994, now abandoned, which is a continuation-in-part of both U.S. patent application Ser. No. 08/279,291, filed Jul. 22, 1994, now U.S. Pat. No. 5,552,550, and U.S. patent application Ser. No 08/279,339, filed Jul. 22, 1994 now U.S. Pat. No. 5,571,919.

TECHNICAL FIELD OF THE INVENTION

The present invention relates to methods of preparing known and new dimeric arylisoquinoline alkaloids. In complement to other methods, the present invention provides more efficient or otherwise advantageous access to a broader range of medically useful compounds The present invention also relates to new dimeric arylisoquinoline compounds and derivatives thereof.

BACKGROUND OF THE INVENTION

Novel compounds exhibiting impressive antiviral and/or antiparasitic properties have recently been described (Manfredi et al., *J Med. Chem.*, 34, 3402–3405 (1991); Bringmann et al., *Angew. Chem. Int. Ed. Eng.*, 32, 1190–1191 (1993); Boyd et al., *J. Med. Chem.*, 37, 1740–1745 (1994); Boyd et al., U.S. Pat. No 5,455,251; Bringmann et al., *Tetrahedron*, 50, 7807–7815 (1994a); Hallock et al., *J. Org. Chem.*, 59, 6349–6355 (1994); Bringmann et al., *Heterocycles*, 39, 503–512 (1994b); Bringmann et al., *Tetrahedron*, 50, 9643–9648 (1994c); Francois et al., *Phytochemistry*, 35, 1461–1464 (1994); Francois et al., PCT Application PCT/US95/01717; Boyd et al., U.S. Pat. No. 5,409,938; Bringrmann et al., U.S. Pat. No. 5,552,550; and Bringmann et al., U.S. patent application Ser. No. 08/279,339). These compounds are members of a general class known as naphthylisoquinoline alkaloids (Bringmann, *The Alkaloids*, Vol. 29 (Brossi, ed.), Academic Press, New York, 1986, pp. 141–184), and can further be characterized based on their structure as either monomeric alkaloids (or "monomers") or dimeric alkaloids (or "dimers").

Monomeric alkaloids include korupensamines or related monomeric naphthylisoquinoline alkaloids and derivatives thereof, which typically possess a C-8' to C-5 naphthalene/isoquinoline linkage, and non-korupensamines or other monomeric naphthylisoquinoline alkaloids and derivatives thereof, which typically lack a C-8' to C-5 naphthalene/isoquinoline linkage.

Dimeric alkaloids include michellamines, which, based on their molecular structure, are comprised of two monomeric alkaloids coupled together (e.g., two monomeric or molecular "halves"). Furthermore, a given michellamine may be either "homodimeric" (comprised of two monomeric halves which are the same) or "heterodimeric" (comprised of two monomeric halves which are different).

Dimeric naphthylisoquinoline alkaloids, as exemplified by the michellamines, have highly desirable and eminently useful medicinal properties that for the most part are distinct from the properties of the monomeric naphthylisoquinoline alkaloids which comprise their molecular halves. For example, the michellamines, such as michellamine B (Boyd et al., U.S. Pat. No. 5,455,251; and Boyd et al. (1994), supra) are highly effective inhibitors of the replication and resultant destructive effects of the human immunodeficiency virus (HIV) in human immune cells. The range of anti-HIV activity observed for these dimeric alkaloids is exceptionally broad, encompassing both the major viral types, HIV-1 and HIV-2, as well as diverse HIV strains, and can be observed in different host cells (Boyd et al. (1994), supra)

Moreover, the dimeric alkaloids would appear to comprise a novel antiviral drug class in that the mechanism of action of the michellamines is distinct from any mechanism previously described. Specifically, the mechanism involves at least two components: (1) an inhibition of the viral reverse transcriptase, and (2) an inhibition of the cell-cell fusion process (McMahon et al., *Antimicrob. Agents Chemother.*, 39, 484–468 (1995)). This suggests that the dimeric alkaloids may prove effective not only in the prevention of nascent viral infection, but also in the prevention of the replication and spread of the virus in vivo and in the prevention of syncytia formation, which has been observed in vitro and which may mediate the depletion of T4 immune cells, which occurs in vivo.

In addition to the medicinally desirable properties of the dimeric alkaloids, they are also quite attractive from a pharmacological and toxicological standpoint In vivo doses of michellamine B that are non-toxic result in a level of the drug in the blood which is well in excess of its effective antiviral concentration (Supko et al., *Anal. Biochem.*, 216, 52–60 (1994); and Supko et al., *Antimicrob. Agents Chemother.*, 39, 9–14 (1995)).

In contrast, the monomeric naphthylisoquinoline alkaloids appear to be devoid of anti-HIV activity. However, the monomeric alkaloids instead have potent antiparasitic properties as exhibited by their activity against strains of malaria-causing organisms. In this respect, it is interesting to speculate that a trace of this antiparasitic activity may be imparted to the alkaloid dimer by its constituent monomeric halves, as a few of the dimeric naphthylisoquinoline alkaloids (e.g., the michellamines) also appear weakly antiparasitic (Boyd et al., U.S. Pat. No. 5,409,938; Frangois et al., PCT Application PCT/US95/01717; Francois et al. (1994), supra).

Unfortunately, attempts by researchers to maximally exploit the potential of the dimeric alkaloids through development of antiviral and antiparasitic therapy and unprecedented uses for the alkaloids have been hindered by the lack of significant access to the dimeric alkaloids. To date, the only known natural source of the dimeric alkaloids is the rare tropical vine *Ancistrocladus korupensis* of Central Africa (Thomas and Gereau, *Novon*, 3, 494–498 (1993); Boyd et al. (1994), supra; and Hallock et al. (1994), supra). The U.S. National Cancer Institute has actively solicited the research community to engage in efforts to discover methods of synthesis of these compounds, as well as synthesis of improved compounds (Anonymous, *J. Nat. Prod.*, 55, 1018–1019 (1992)).

To address the critical need for synthetic access to michellamines and other medically useful known and new dimeric naphthylisoquinoline alkaloids, a recent, previous invention provided a method of preparation of such compounds by the coupling together of two selected synthetic or naturally occurring monomeric naphthylisoquinoline alkaloids (Bringmann et al., U.S. patent application Ser. No. 08/279,339). More specifically, the previous invention provided a method of preparing a naphthylisoquinoline alkaloid dimer comprising the steps of (a) selecting first and second naphthylisoquinoline alkaloid monomers, which are either the same or different, (b) optionally introducing protective group(s) at desired site(s) in the monomers, (c) introducing activation group(s) at the desired coupling site(s) of the monomers if needed for coupling of the monomers, (d) coupling the first and second monomers to form a dimeric naphthylisoquinoline alkaloid, and (e) optionally removing the protective group(s) from the dimeric naphthylisoquinoline alkaloid.

Thus, in the method of the previous invention, the preselected or pre-constructed naphthylisoquinoline monomers, each of which already contains a naphthalene-to-isoquinoline linkage, are coupled together to form the central biaryl axis (naphthalene-to-naphthalene) comprising the dimer. For any particular dimeric compound needed or sought by synthesis, however, an alternate method of preparation providing more efficient or otherwise advantageous access to the naphthylisoquinoline alkaloid dimer would be highly desirable and useful. It would be particularly desirable, for example, to have an alternate method, which does not require the use of pre-selected or pre-constructed monomeric naphthylisoquinoline monomers, which may not be immediately or efficiently available. An alternate method providing access not only to known dimeric naphthylisoquinoline alkaloids but also to unprecedented new dimeric arylisoquinolines would be even more desirable.

Accordingly, it is an object of the present invention to provide a new method for synthesizing dimeric arylisoquinoline alkaloids. The distinct novelty of the synthetic strategy is the intermolecular biaryl coupling of intact isoquinoline building blocks to the biaryl centerpiece comprising the desired dimeric product This synthetic strategy bears some similarities to that disclosed in the method of yet another previous invention, which incorporates the intermolecular biaryl coupling of an isoquinoline building block with a naphthalene building block to form a monomeric naphthylisoquinoline alkaloid (Bringmann et al., U.S. Pat. No. 5,552,550). This and other objects and advantages of the present invention, as well as additional inventive features, will be apparent from the description of the invention provided herein.

BRIEF SUMMARY OF THE INVENTION

The present invention provides a method of preparing a dimeric naphthylisoquinoline alkaloid comprising (a) obtaining first and second isoquinoline building blocks, which are either the same or different, each having protective group(s) at desired site(s), each containing an activation group at a desired coupling site, and each being a tetrahydroisoquinoline, dihydroisoquinoline, or fully aromatic isoquinoline building block, (b) obtaining a biaryl building block having protective group(s) at desired site(s), a first activation group at a first desired coupling site, and a second activation group at a second desired coupling site, (c) coupling the first isoquinoline building block at the desired first coupling site, (d) coupling the second isoquinoline building block at the second coupling site of the biaryl building block, and (e) optionally deprotecting desired site(s) on the biaryl building block.

The present invention also provides new dimeric arylisoquinoline alkaloids, as well as derivatives thereof.

BRIEF DESCRIPTION OF THE DRAWINGS

FIG. 7A shows examples for preparation of electrophilic isoquinoline building blocks; typical reaction conditions are: a) $Br_2$, tert-$BuNH_2$, toluene; b) BnBr, $K_2CO_3$, acetone; c) BnBr, $K_2CO_3$, acetone; d) $Br_2$, $CH_2Cl_2$; e) $Tf_2O$, TlOEt, $CH_2Cl_2$. FIG. 7B shows examples for preparation of nucleophilic isoquinoline building blocks; typical reaction conditions are; a) BnBr, $K_2CO_3$, acetone; b) n-BuLi, -78° C., THF; c) $B(OMe)_3$, THF, aqueous workup; d) BnBr, $K_2CO_3$, acetone; e) $Br_2$, DMEF; f) n-BuLi, -78° C., THF; g) $B(OMe)_3$, aqueous workup.

FIGS. 9A–9D show symmetrical homodimers, wherein the central biaryl core is a binaphthalene or biphenyl, and the isoquinoline parts are identical; FIGS. 9E–9G show nonsymmetrical heterodimers, wherein the isoquinoline parts are not identical and/or wherein the central biaryl core is nonsymmetrical (e.g., such as a phenylnaphthalene).

DETAILED DESCRIPTION OF THE INVENTION

Figure 1A:
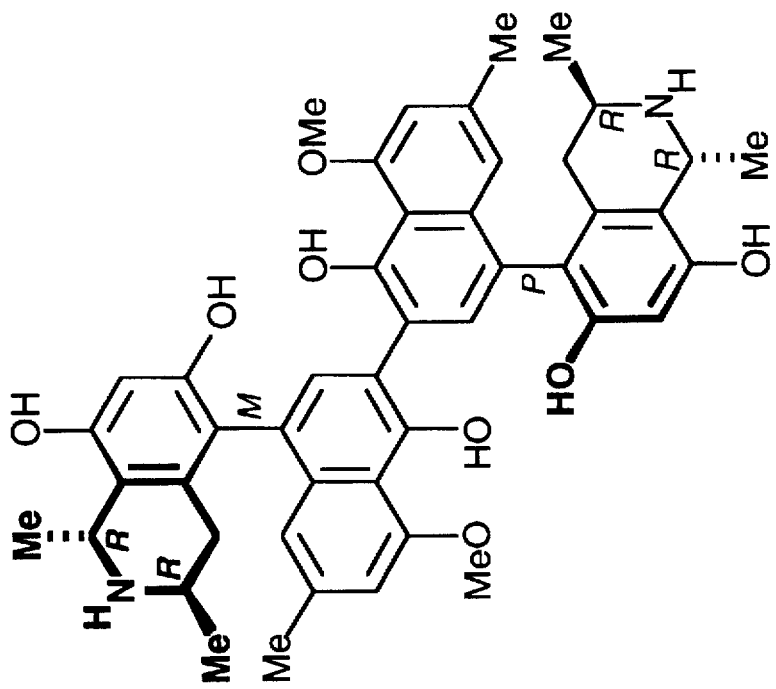
FIG. 1 illustrates the structures of michellamine A (1a) and michellamine B (1b).

The present invention provides methods of preparing both known and new dimeric arylisoquinoline alkaloids and derivatives thereof. The present invention also provides new dimeric arylisoquinoline compounds and derivatives thereof.

Definitions

For clarification of the chemical structures described herein, the following definitions apply.

By arylisoquinoline homodimer is meant a dimeric alkaloid containing two monomeric arylisoquinoline halves, wherein each half is the same.

By arylisoquinoline heterodimer is meant a dimeric alkaloid containing two monomeric arylisoquinoline halves, wherein each half is different By $C_1$–$C_6$ alkyl is meant straight or branched-chain $C_1$–$C_6$ alkyl groups. Examples include, but are not limited to, methyl, ethyl, n-propyl, isopropyl, n-butyl, isobutyl, sec-butyl, tertiary-butyl, n-pentyl, isopentyl, and n-hexyl.

By aryl is meant an organic radical derived from an aromatic hydrocarbon Examples of aryl groups include phenyl, o-, m-, and p-hydroxyphenyl, and naphthyl.

By aliphatic is meant an organic radical derived from an open hydrocarbon chain Examples of aliphatic radicals include alkanes, alkenes, and alkynes. Specific examples of aliphatic radicals, which can be used in the present invention, include, but are not limited to, $C_1$–$C_6$ alkyl radicals, straight or branched.

Medical and Other Uses

The new dimeric arylisoquinoline alkaloids and derivatives thereof are expected to have at least those medicinal properties possessed by the previously known dimeric naphthylisoquinoline alkaloids (see, e.g., Boyd et al., U.S. Pat. No. 5,455,251; and Boyd et al., (1994), supra). However, depending upon the particular disease and host to be treated, a compound of the present invention will be distinctly advantageous in a given situation.

Medically useful properties of the compounds of the present invention can be readily confirmed by one knowledgeable and skilled in the art by use of any of a variety of methods which have been published or otherwise disclosed elsewhere. For example, antiviral properties, particularly anti-HIV properties, can be confirmed as described in Boyd et al. (1994), supra, and Boyd et al., U.S. Pat. No. 5,455,251. Also, for example, in vitro and in vivo antimalarial activity may be confirmed as described in Frangois et al., *Phytochemistry*, 35, 1461–1464 (1994), Gulakowski et al., *J. Virol. Methods*, 33, 87–100 (1991), Francois et al., PCT Application PCT/US95/01717; and Boyd et al., U.S. Pat. No. 5,409,938.

The compounds of the present invention are also useful in a variety of in vitro applications. Such in vitro applications include biochemical assays, as well as chemical syntheses and viral research.

Synthesis of Dimeric Arylisoguinoline Alkaloids

The present inventive method of preparing a dimeric arylisoquinoline alkaloid comprises the steps of:

(a) obtaining first and second isoquinoline building blocks, which are either the same or different, each having protective group(s) at desired site(s), each containing an activation group at a desired coupling site, and each being a tetrahydroisoquinoline, dihydroisoquinoline, or fully aromatic isoquinoline building block.

(b) obtaining a biaryl building block having protective group(s) at desired sites), a first activation group at a first desired coupling site, and a second activation group at a second desired coupling site, (c) coupling the first isoquinoline building block at the desired first coupling site, (d) coupling the second isoquinoline building block at the second coupling site of the biaryl building block, and (e) optionally deprotecting desired site(s) on the biaryl building block.

While the foregoing steps can be utilized to prepare a dimeric arylisoquinoline alkaloid in accordance with the present invention, the order of several of the aforesaid steps of the present inventive method are not critical. For example, the first and second isoquinoline building blocks can be simultaneously coupled to the biaryl building block. Alternatively, the second activation group can be introduced at the second desired coupling site in the biaryl building block after the first isoquinoline building block is coupled to the biaryl building block, with the second isoquinoline building block being coupled to the biaryl building block after the first isoquinoline building block is coupled to the biaryl building block. In that instance, the desired site(s) on the biaryl building block can be deprotected prior to introducing the second activation group at the second desired coupling site in the biaryl building block.

Preferably, the present inventive method further comprises:

(f) removing the protective groups from the dimeric arylisoquinoline alkaloid, and (g) purifying the dimeric arylisoquinoline alkaloid.

When the first and second isoquinoline building blocks are the same, then their coupling to a symmetrical biaryl building block results in a homodimeric arylisoquinoline alkaloid. Alternatively, when the first and second isoquinoline building blocks are different, then their coupling to a symmetrical biaryl building block results in a heterodimeric arylisoquinoline alkaloid. The coupling of same or different first and second isoquinoline building blocks to a nonsymmetrical biaryl building block also results in a heterodimeric arylisoquinoline alkaloid.

Any suitable building blocks can be utilized. The isoquinoline building blocks can have the configurations at any chiral centers as desired in the dimeric arylisoquinoline alkaloid. For example, when the isoquinoline building block is a tetrahydroisoquinoline building block, the tetrahydroisoquinoline building block might preferably have methyl groups at C-1 and C-3, and these chiral centers might preferably have the R-configuration at C-1 and the R-configuration at C-3, the S-configuration at C-1 and the R-configuration at C-3, the R-configuration at C-1 and the S-configuration at C-3, or the S-configuration at C-1 and the S-configuration at C-3. Similarly, when the isoquinoline building block is a dihydroisoquinoline building block, the dihydroisoquinoline building block might preferably have a methyl group at C-3 and might preferably have either the S-configuration or the R-configuration at C-3. The biaryl building block can be any suitable symmetrical biaryl building block, such as, for example, a binaphthalene or a biphenyl, or it might be a nonsymmetrical biaryl building block, such as phenylnaphthalene.

Any suitable activation and protective groups can be utilized with respect to any of the building blocks. One or both of the activation groups, used either on the biaryl or on the first and second isoquinoline building blocks, will generally be a nucleophilic activation group, while the other of the activation groups, on the other building block(s), will generally be an electrophilic activation group The first and second activation groups for the biaryl building block are preferably electrophilic activation groups. The activation groups for the first and second isoquinoline building blocks are preferably nucleophilic activation groups. The nucleophilic activation groups are preferably selected from the group consisting of boronic acid and trialkylstannyl groups. The electrophilic activation groups are preferably selected from the group consisting of halogens, particularly bromine, and O-triflate leaving groups Introduction of the activation group may be accomplished by any suitable means, for example, by metallation followed by conversion to an activation group, such as trialkylstannyl or a boronic acid derivative Protective groups are preferably selected from the group consisting of benzyl, acyl, formyl, and isopropyl groups In the aforementioned method, when the first and second isoquinoline building blocks are the same, the couplings of the first and second isoguinoline building blocks to the biaryl building block are preferably done simultaneously (e.g., in one step using two equivalents of the isoquinoline building block and one equivalent of the biaryl building block) If the first and second isoquinoline building blocks are different, then, optionally, the suitably activated and protected first isoquinoline building block may be coupled to the suitably activated and protected biaryl building block; then, optionally, any protective group(s) is (are) removed as necessary, and the second activation group is introduced at the desired coupling site, followed by coupling of the suitably activated and protected second isoquinoline building block.

The aforementioned process steps can be carried out by any suitable means. Thus, for example, the coupling can be effected by several means, such as by transition metal catalysis, especially by using Pd. Also, the dimeric arylisoquinoline alkaloid can be purified by a variety of means, preferably by HPLC The purification of the dimeric arylisoquinoline alkaloid is more preferably carried out by HPLC on an amino-bonded or other phase column so as to obtain a pure atropodiastereomer. Moreover, while the purification process is preferably carried out after removal of the protective groups, the purification process can be carried out either before or after the removal of the protective groups.

Figure 1B:
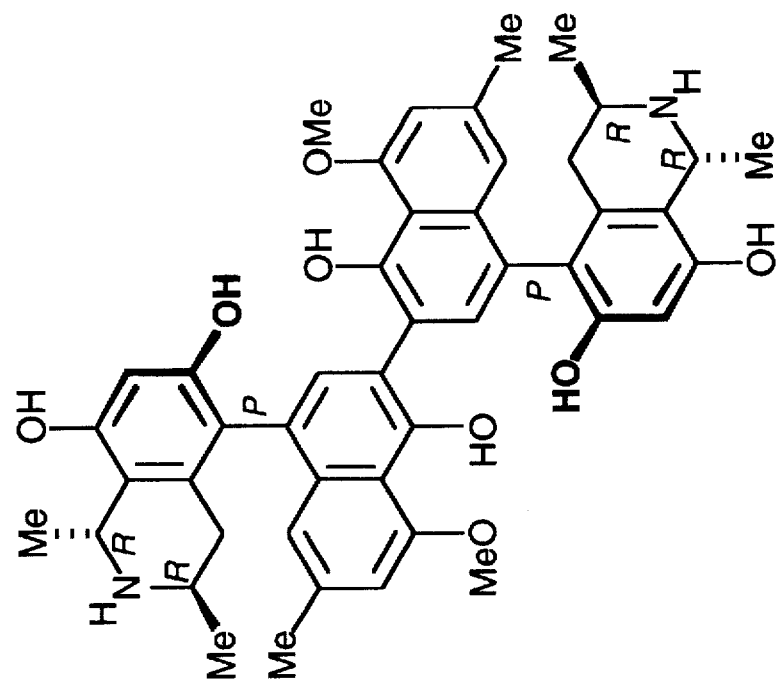

The protective group(s) can be removed from the dimeric arylisoquinoline alkaloid by any suitable means, preferably by using methanolic HCl and by hydrogenolysis. Also, following synthesis, the dimeric arylisoquinoline alkaloid can be purified by any suitable means, preferably by HPLC, and especially on an amino-bonded or other phase column Accordingly, the method of the present invention can be used to obtain any of the dimeric arylisoquinoline compounds of previous inventions, in particular those disclosed in U.S. Pat. No. 5,455,251 (Boyd et al.) and U.S. patent application Ser. No. 08/279,339 (Bringmann et al.). Michellamines A and B (1a and 1b, respectively, in FIG. 1) are examples of such compounds. The michellamines are a type of dimeric arylisoquinoline alkaloid in which the biaryl core is a binaphthalene. The synthesis of michellamines A and B provides a more specific illustration of the method of the present invention.

Synthesis of Michellamines

Michellamines A and B have identical 1R,3R-configured tetrahydroisoquinoline parts, but differ with respect to the configurations at the biaryl axes (Boyd et al (1994), supra; Bringmann et al. (1993), supra; Bringmann et al. (1994a), supra; and Bringmann et al. (1994c), supra). Curiously, the third possible atropoisomer, michellamine C, does not appear to co-occur naturally, although equilibration of 1a and 1b produces a mixture of all three michellamines A, B, and C (Boyd et al (1994), supra). With the central axis not being configurationally stable, michellamines A, B and C constitute the complete series of atropodiastereomers with respect to the stereogenic axes between the isoquinoline and the naphthalene parts. A recently disclosed (Bringmann et al. (1994c), supra) first total synthesis of michellamine A (1a) was accomplished by the method of a previous invention (Bringmann et al., U.S. patent application Ser. No. 08/279, 339) by oxidative coupling of the appropriately protected corresponding monomeric naphthylisoquinoline alkaloid, named korupensamine A (Hallock et al. supra), which itself had also been synthesized (Bringmann et al. (1994b), supra). In the method of the present invention, the non-biomimetic total synthesis of both michellamines A and B can be accomplished by a complementary stepwise construction of the biaryl axes, forming first the (configurationally unstable) central axis and then, simultaneously, the two (stereogenic) outer ones. A more specific illustration of the method follows below Given the constitutionally symmetric structure of the michellamines, the preferable synthesis of these particular compounds comprises the double intermolecular coupling of a central binaphthalene building block with two equivalents of an appropriately protected, enantiomerically pure tetrahydroisoquinoline building block The synthesis is outlined in FIGS. 2 and 3. For the required binaphthalene unit 6, acetate groups are selected for the protection of the O-functionalities and triflate groups for the activation of the coupling positions.

The preparation of the binaphthalene building block 6 starts with the known (Casey et al., *J. Org. Chem.*, 46, 2089–2092 (1981); Savard and Brassard, *Tetrahedron*, 40, 3455–3464 (1984)) diene 3, available in one step from methyl 3,3-dimethyl-acrylate by successive treatment with lithium diusopropylamide and trimethylsilyl chloride. The 2,6-dibromobenzoquinone (2) is prepared by the oxidation of 2,4,6-tribromophenol with fuming nitric acid (Hodgson et al., *J. Chem. Soc.*, 1085–1087 (1930)); a $CH_2Cl_2$ solution of the crude is passed through a column of silica gel. The Diels-Alder reaction of 3 with 2 proceeds regiospecifically, as expected from Savard and Brassard ((1984), supra) to give, after aromatization of the adduct, a hydroxynaphthoquinone, which is converted to its methyl ether 4. This is then dimerized using copper bronze (Shimizu et al., *Tetrahedron Lett.*, 34, 3421–3424 (1993)) and reductively acetylated (Farina et al., *Tetrahedron*, 38, 1531–1537 (1982)) to afford tetraacetate 5. An alternate synthesis of the intermediate diquinone (not shown; intermediate between 4 and 5) may be prepared according to Laatsch (*Liebigs Ann. Chem.*, 1321–1347 (1980)). The two less-hindered acetate groups in 5 are selectively cleaved by treatment with diazabicycloundecene (DBU) in methanol (Baptistella et al., *Synthesis*, 436–439 (1989)) to generate a diol, which is converted to ditriflate using $Tf_2O$ in $CH_2Cl_2$ and 2,6-lutidine as a base.

Figure 3:
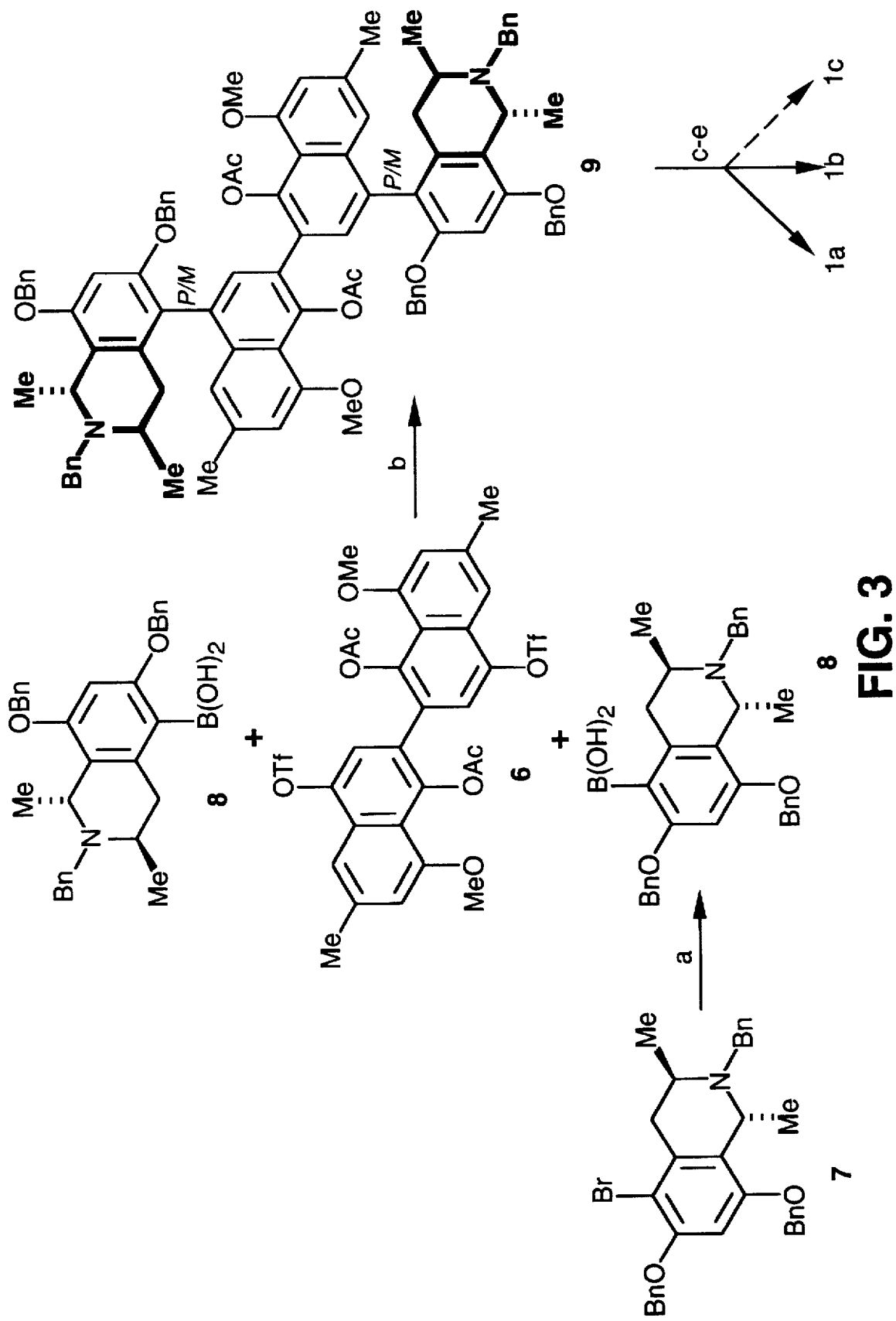
FIG. 3 illustrates the selection and further preparation of suitably protected and activated isoquinoline building block (s), their coupling to the biaryl building block (6), and subsequent deprotection and separation of the product michellamines (1a and 1b of FIG. 1). Reaction conditions: a) n-BuLi, THF, $B(OMe)_3$, -78° C. to rt, aqueous workup, 89%; b) $Pd(PPh_3)_4$, $Ba(OH)_2$, $DME/H_2O$, 80° C., 8 h, 74%; c) $H_2$, Pd/C (10%), 1 atm, EtOH, 3d; d) methanolic HCl, reflux 10 h, 85% from 9; e) atropoisomer separation as reported previously (Boyd et al., *J. Med. Chem.*, 37, 1740–1745 (1994)).

The next steps are the selection and coupling of the isoquinoline building blocks. With the central biaryl axis thus established in the biaryl building block, and the required coupling positions therein activated by O-triflate substituents, the construction of the outer biaryl axes is then approached. The steps are illustrated in FIG. 3. As suitable building block(s) for the particular heterocyclic tetrahydroisoquinoline system comprising the michellamines, the correctly configured, enantiomerically pure boronic acid 8, having benzyl group protection for the O- and the N-functionalities, is selected. This building block is prepared from the known (Bringmann et al. (1994b), supra) corresponding bromo compound 7, by lithiation and treatment with freshly distilled B(OMe)$_3$, followed by aqueous workup. Reaction of 6 and 8 in the presence of Pd(PPh$_3$)$_4$ and Ba(OH)$_2$, in DME/H$_2$O as a solvent (Watanabe et al., *Synlett.*, 207–210 (1992); Suzuki, *Pure Appl. Chem.*, 213–222 (1994)), provides the quateraryl 9, with all the ring systems correctly linked to each other, as a mixture of atropodiastereomers. Removal of all O- and N-protecting groups finally yields a mixture of the atropodiastereomeric michellamines 1a and 1b, which can then be resolved, if desired, as described previously (Manfredi et al. (1991), supra; and Boyd et al. (1994), supra). The synthetic 1a and 1b can readily be shown to be identical, by direct comparison, to authentic, naturally derived materials. More specific details of a synthesis of michellamines A and B, illustrating further the present invention, are provided in Example 1.

Synthesis of Derivatives and Other Modified Dimeric Arylisoquinoline Alkaloids

One skilled in the art will readily appreciate that certain chemical modifications can be incorporated as desired into the method of the present invention, and/or can be used to modify the end product thereof, to obtain a useful synthetic dimeric arylisoquinoline alkaloid derivative Such modified properties can include greater therapeutic potency against a particular disease or disease-causing organism, a broader spectrum of therapeutic activity against diverse diseases or disease-causing organisms, enhanced oral bioavailability, less toxicity in a particular host mammal, more advantageous pharmacokinetics and/or tissue distribution in a given host mammal, and the like. For example, by applying one or more well known chemical reactions (such as exemplified in previous disclosures (Boyd et al., U.S. Pat. No. 5,455,251; and Bringmann et al., U.S. patent application Ser. No. 08/279,339) to a given dimeric arylisoquinoline alkaloid, prepared according to the aforementioned method, a useful new derivative may be obtained, wherein one or more phenolic hydroxyl group(s) may instead be replaced by an ester, sulfonate ester, or ether group, one or more methyl ether group(s) may instead be replaced by a phenolic hydroxyl group, one or more phenolic hydroxyl group(s) may instead be replaced by an aromatic hydrogen substituent, a secondary amine site may instead be replaced by an amide, sulfonamide, tertiary amine, or alkyl quaternary ammonium salt or corresponding Hoffmann elimination product thereof, a tertiary amine site may instead be replaced by a secondary amine, and one or more aromatic hydrogen substituent(s) may instead be replaced by a halogen, nitro, amino, hydroxyl, thiol, acyl, C$_1$–C$_6$ alkyl, or cyano substituent, and CH$_3$ may be replaced by H. Alternatively, if a "modified" dimeric alkaloid is desired, such modifications can be contained or incorporated within the isoquinoline and/or biaryl building blocks used to synthesize the dimer. For example, a useful modified compound can be obtained by the method of the present invention by selecting and constructing, and incorporating in the coupling step(s), an appropriately protected and activated tetrahydroisoquinoline, dihydroisoquinoline, or fully aromatic isoquinoline building block, having any desired different configurations at any present chiral center(s), and having any desired different substituent(s) at any available ring position(s). Further illustrations of obtaining different biaryl and isoquinoline building blocks are given in Examples 2 and 3, respectively.

Synthesis of Novel Dimeric Arylisoquinoline Alkaloids and Derivatives

Given the present disclosure, it will be apparent to one skilled in the art that unprecedented new useful dimeric arylisoquinoline compounds can be prepared by the method of the present invention. For example, variations in either or both of the isoquinoline building blocks and/or in the biaryl building block may be incorporated in the method to give unprecedented compounds. In particular,: variations in the biaryl building block can be incorporated into the method to make new dimers, which lack the central binaphthalene core comprising the heretofore known group of dimeric arylisoquinoline alkaloids, and instead contain a different biaryl central core of either a symmetrical or nonsymmetrical nature. For example, such novel dimeric compounds can be prepared by the method of the present invention by use of an appropriately protected and activated biphenyl or phenylnaphthalene building block, respectively.

Novel Dimeric Arylisoquinoline Alkaloids and Derivatives

Accordingly, the present invention also provides a new dimeric arylisoquinoline alkaloid compound, wherein the central core is comprised of a biphenyl or a phenylnaphthalene. More specifically, the present invention provides a dimeric arylisoquinoline compound comprised of first and second arylisoquinoline monomer halves, which are the same or different, wherein the first and second monomer halves have the formula (minus an H at the coupling point):

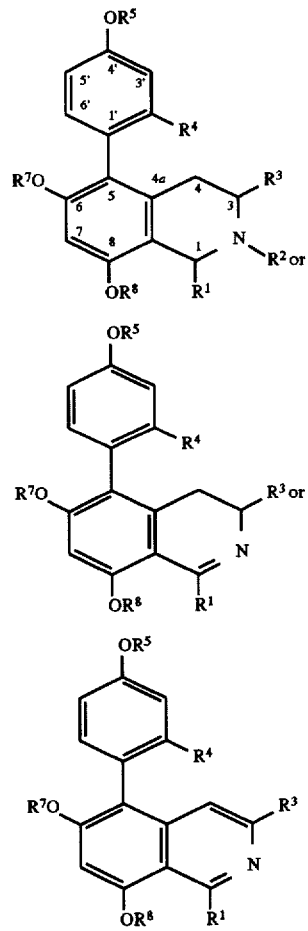

wherein R$^1$, R$^3$, and R$^4$ may be the same or different and each may be H or C$_1$–C$_6$ alkyl, R$^2$, R$^5$, R$^7$, and R$^8$ may be the same or different and each may be H, C$_1$–C$_6$ alkyl, $R^9CH_2$—, $R^9CO$—, or $R^9SO_2$, $R^9$ may be H, $C_1$–$C_6$ alkyl or aryl, and one or more of the ring positions 1, 3, 4, 2', 3', 4', 5', 6', 6, 7, and 8 instead may be substituted with halo, nitro, amino, hydroxyl, thiol, acyl, $C_1$–$C_6$ alkyl, or cyano, one or more phenolic hydroxyl group(s) may instead be an ester, sulfonate ester, or ether group, one or more methyl ether group(s) may instead be a phenolic hydroxyl group, one or more phenolic hydroxyl group(s) may instead be an aromatic hydrogen substituent, one or more secondary amine site(s) may instead be an amide, sulfonamide, tertiary amine, alkyl quaternary ammonium salt or corresponding Hoffmann elimination product thereof, and one or more tertiary amine site(s) may instead be a secondary amine.

The present invention also more specifically provides a dimeric arylisoquinoline compound comprised of coupled first and second arylisoquinoline monomer halves, wherein the first monomer half has the formula (minus an H at the coupling point):

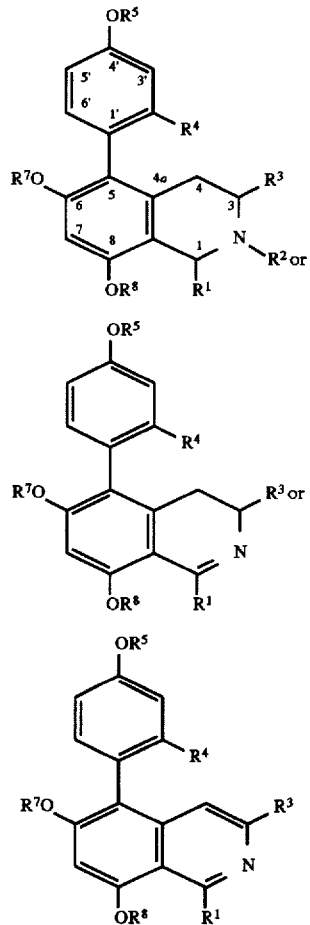

wherein $R^1$, $R^3$, and $R^4$ may be the same or different and each may be H or $C_1$–$C_6$ alkyl, $R^2$, $R^5$, $R^7$, and $R^8$ may be the same or different and each may be H, $C_1$–$C_6$ alkyl, $R^9CH_2$—, $R^9CO$—, or $R^9SO_2$, $R^9$ may be H, $C_1$–$C_6$ alkyl or aryl, and one or more of the ring positions 1, 3, 4, 2', 3', 4', 5', 6', 6, 7, and 8 instead may be substituted with halo, nitro, amino, hydroxyl, thiol, acyl, $C_1$–$C_6$ alkyl, or cyano, one or more phenolic hydroxyl group(s) may instead be an ester, sulfonate ester, or ether group, one or more methyl ether group(s) may instead be a phenolic hydroxyl group, one or more phenolic hydroxyl group(s) may instead be an aromatic hydrogen substituent, one or more secondary amine site(s) may instead be an amide, sulfonamide, tertiary amine, alkyl quaternary ammonium salt or corresponding Hoffmann elimination product thereof, and one or more tertiary amine site(s) may instead be a secondary amine, and the second monomer half has the formula (minus an H at the coupling point):

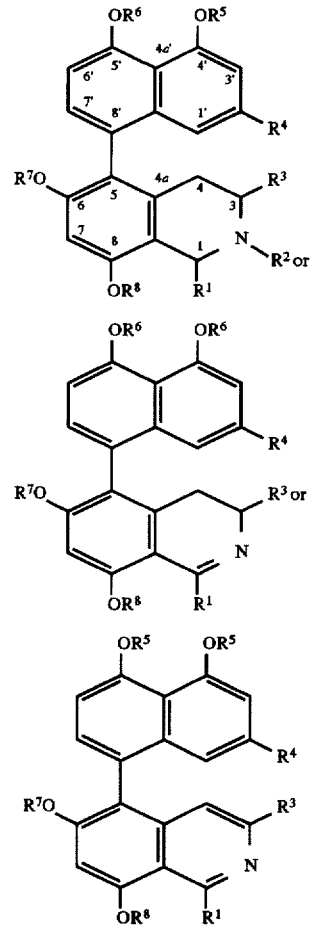

wherein $R^1$, $R^3$, and $R^4$ may be the same or different and each may be H or $C_1$–$C_6$ alkyl, $R^2$, $R^5$, $R^6$, $R^7$, and $R^8$ may be the same or different and each may be H, $C_1$–$C_6$ alkyl, $R^9CH$—, $R^9CO$—, or $R^9SO_2$—, $R^9$ may be H, $C_1$–$C_6$ alkyl or aryl, and one or more of the ring positions 1, 3, 4, 1', 2', 3', 4', 5', 6', 7', 6, 7, and 8 may instead be substituted with halo, nitro, amino, hydroxyl, thiol, acyl, $C_1$–$C_6$ alkyl, or cyano, one or more phenolic hydroxyl group(s) may instead be an ester, sulfonate ester, or ether group, one or more methyl ether group(s) may instead be a phenolic hydroxyl group, one or more phenolic hydroxyl group(s) may instead be an aromatic hydrogen substituent, one or more secondary amine site(s) may instead be an amide, sulfonamide, tertiary amine, alkyl quaternary ammonium salt or corresponding Hoffmann elimination product thereof, and one or more tertiary amine site(s) may instead be a secondary amine. Further illustration of the diversity of homodimeric and heterodimeric arylisoquinoline alkaloids that can be made according to the method of the present invention is given in Example 5.

EXAMPLES

The following examples further illustrate the present invention, but, of course, should not be construed as in any way limiting its scope.

Example 1:

Synthesis of Michellamines A and B

This example provides a more detailed description of the synthesis of michellamines A and B (FIG. 1) according to the method of the present invention. The synthetic procedure was performed as summarized in FIGS. 2 and 3. Reaction conditions are given in the corresponding figure legends. Further details of key reactions are as follows.

A 17.5 mg (39.5 µmol) sample of the isoquinoline-boronic acid 8, 11.1 mg (14.2 µmol) of the binaphthalene 6, a pinch of Pd(PPh$_3$)$_4$, and 8.3 mg (43.5 µmol) Ba(OH)$_2$ were dissolved under argon in a mixture of 1.5 ml DME and 0.5 ml degassed water. The reaction mixture was heated for 6 h to 80° C., the solvent was removed under reduced pressure, and the residue was purified by preparative thin-layer chromatography (petroleum ether/diethyl ether, 2:1), to afford 15 mg (71%) of the quateraryl 9.

This crude product was dissolved in 2 ml dry MeOH, a pinch Pd/C (10%) was added, and the mixture was hydrogenated for 3 d at ambient pressure. After removal of the solvent, the residue was dissolved in 5 ml methanolic HCl and heated under reflux for 10 h. Removal of the solvent, yielded 7 mg (85%) from 9 of a mixture of the atropoisomeric michellamines A (1a) and B (1b), which were further purified as described previously (Manfredi et al. (1991), supra; and Boyd et al. (1994), supra).

The mp, [α]p, and $^1$H NMR (CDCl$_3$) data for selected new compounds follow. 4: mp 175°–177° C., $^1$H NMR δ7.54 (s, 1H), 7.41 (s, 1H), 7.10 (s, 1H), 4.01 (s, 3H), 2.49 (s, 3H); 5: obtained as a gum, $^1$H NMR δ7.22 (s, 2H), 7.12 (br, 2H), 6.72 (s, 2H), 3.89 (s, 6H), 2.49 (s, 6H), 2.43 (s, 6H, 2.12 (br, 6H); 6: mp 190°–191° C., $^1$H NMR δ7.47 (s, 2H), 7.40 (br, 2H), 6.82 (s, 2H), 3.92 (s, 6H), 2.55 (s, 6H), 2.55 (s, 6H), 2.07 (s, br, 6H); 8: mp 106°–108° C., [α]$_D$=+49.3 (c=1.5 in MeOH), $^1$H NMR δ7.31-7.19 (m, 15H), 6.42 (s, 1H), 5.92 (s, br, 2H), 5.04 (s, 2H), 5.02 (s, 2H), 4.08 (q, J=6.7 Hz, 1H), 3.85 (d, J=14.1 Hz, 1H), 3.56-3.45 (m, 1H), 3.33 (d, J=14.1 Hz, 1H), 3.13 (dd, J =18.0, 4.6 Hz, 1H), 2.79 (dd, J=18.0, 11.3 Hz, 1H), 1.35 (d, J=6.7 Hz, 3H), 1.30 (d, J=6.6 Hz, 3H)

Example 2:

Preparation of Various Biaryl Building Blocks

Figure 4:
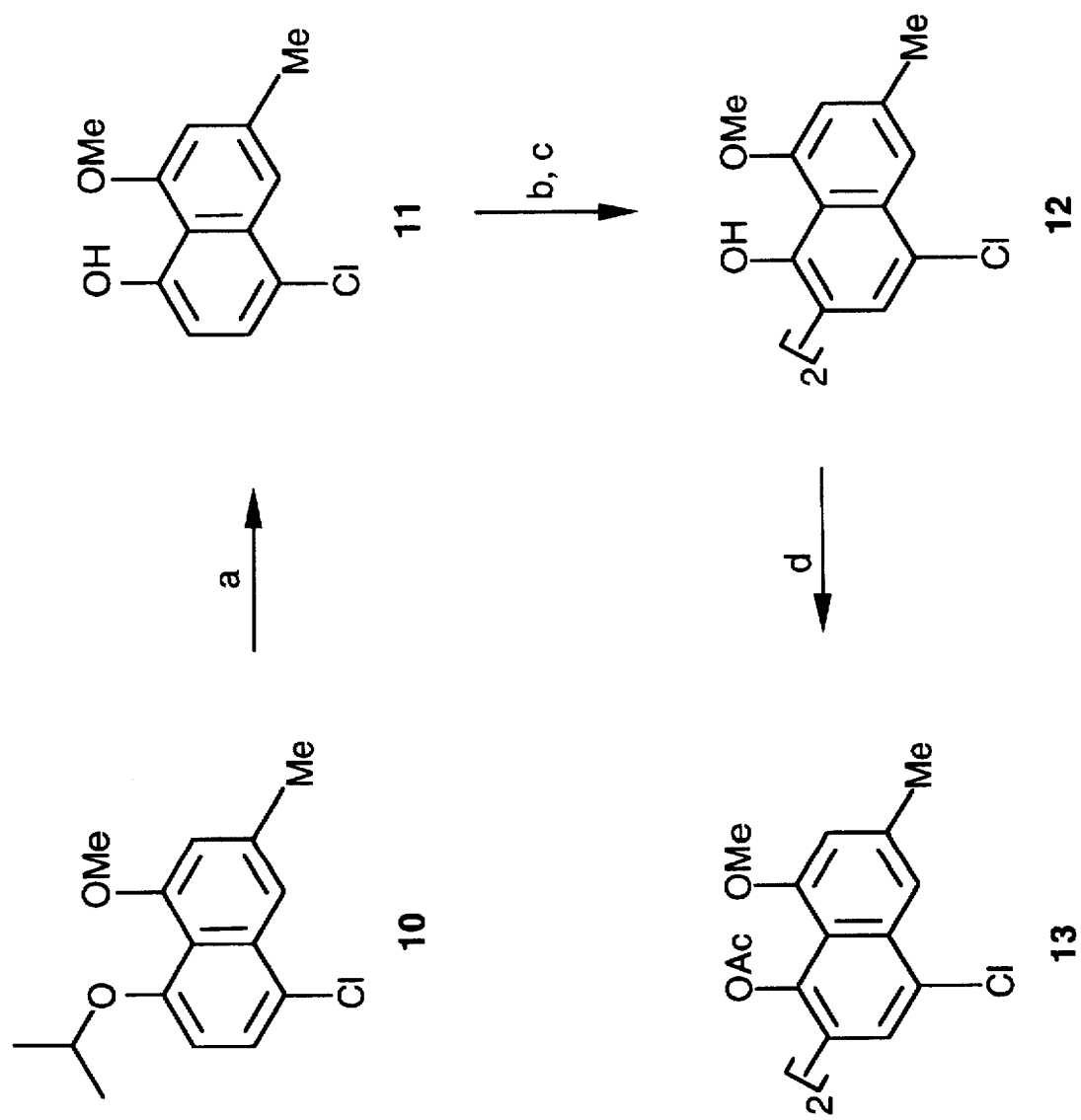
FIG. 4 illustrates the preparation of a biaryl building block by oxidative phenolic coupling. Typical reaction conditions are: a) $BCl_3$, $CH_2Cl_2$; b) $FeCl_3$ $H_3CCN$; c) Zn, HOAc; d) AcCl, $NEt_3$, DMAP, $CH_2Cl_2$.

A variety of different approaches can be used to prepare a wide diversity of biaryl building blocks for use in the method of the present invention. For example, a suitable building block for use in the steps depicted in FIG. 3 for synthesis of michellamines A and B can be prepared by a suitable means different than shown in FIG. 2. In particular, an oxidative phenolic coupling strategy can be used to construct a desired biaryl from two selected aryl "halves"; the strategy is directly analogous to that used to construct the central biaryl axis between two naphthylisoquinoline monomers as disclosed in a previous invention (Bringmann et al., U.S. patent application Ser. No. 08/279,339). Thus, FIG. 4 illustrates the preparation of a suitable biaryl (specifically a binaphthalene) building block by oxidative phenolic coupling of two suitably protected aryl halves, each also containing the activating group desired in the biaryl building block. Typical reaction conditions are shown in the corresponding figure legend. Further details of key reactions typically are as follows.

The naphthalene building block 10, prepared in analogy to the corresponding bromo derivative (Bringmann et al., Heterocycles, 39, 503–512 (1994b)) is de-isoproylated with BCl$_3$ to give the appropriate coupling substrate 11. Oxidative coupling with FeCl$_3$ and subsequent reduction with Zn/HOAc (Laatsch et al., Liebigs Ann. Chem., 319–339 (1984)) gives the dimeric naphthalene 12, which is finally acetylated with AcCl to give the binaphthalene 13. Alternatively, the chlorine can be substituted by bromine on the level of 12 by hydrogenative reduction and subsequent selective bromination with n-Bu$_4$NBr$_3$ in the para position of the free hydroxy function (Berthelot et al., Can. J. Chem., 67, 2061–2066 (1989))

Figure 5A:
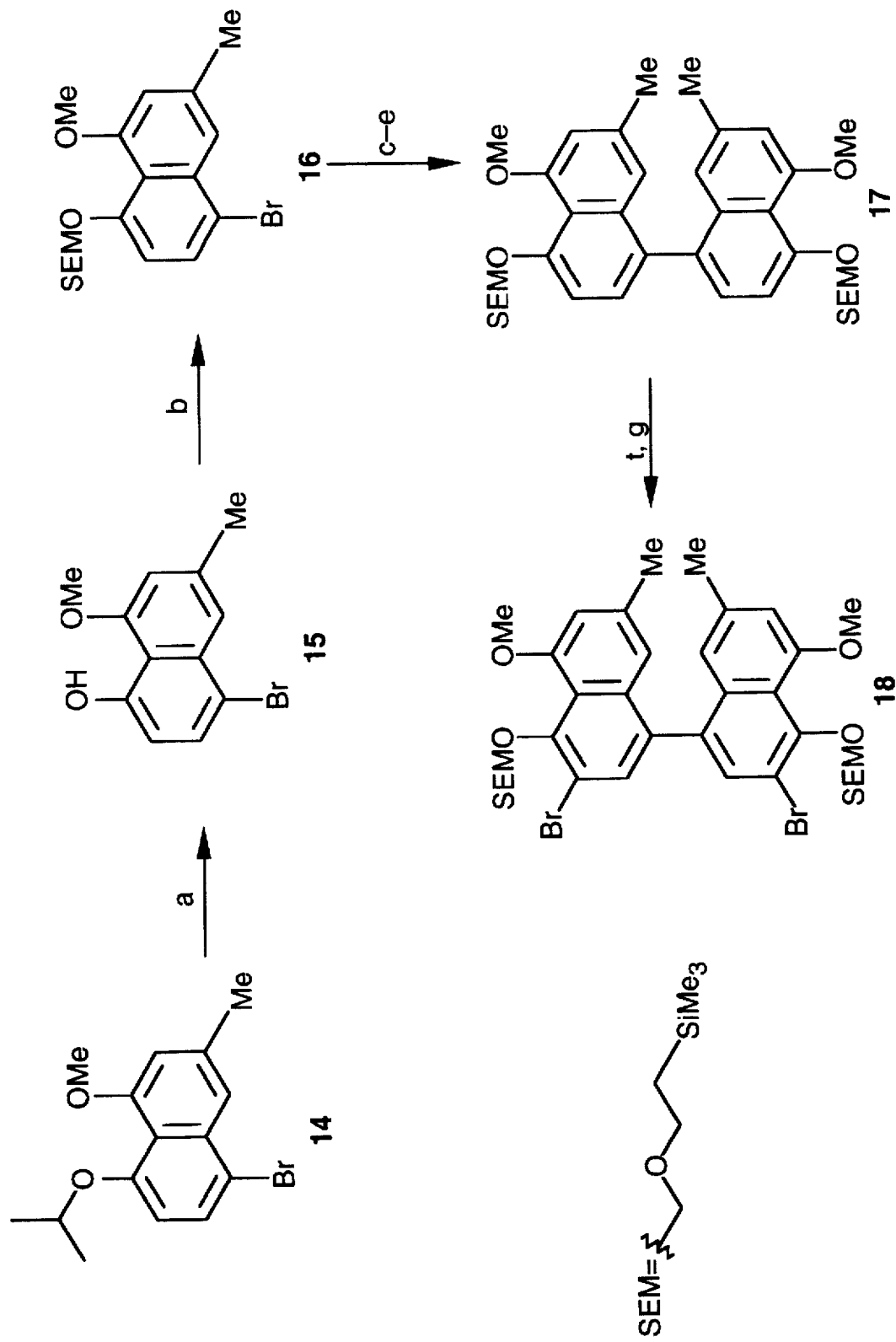
FIGS. 5A–B illustrate other approaches to the preparation of different biaryl building blocks. For FIG. 5A, typical reaction conditions are: a) $BCl_3$, $CH_2Cl_2$; b) SEM-Cl, PTC, 2N NaOH, $CH_2Cl_2$; c) t-BuLi, $Et_2O$, -78° C.; d) CuCN; e) $O_2$, -78° C.; f) t-BuLi, $Et_2O$, -78° C.; g) $C_2Br_2Cl_4$. For FIG. 5B typical reaction conditions are: a) $BCl_3$, $CH_2Cl_2$; b) $Cu(Ac)_2$, $NH_3$, 2,6-xylenol; c) AcCl, $NEt_3$, DMAP, $CH_2Cl_2$.
Figure 5B:
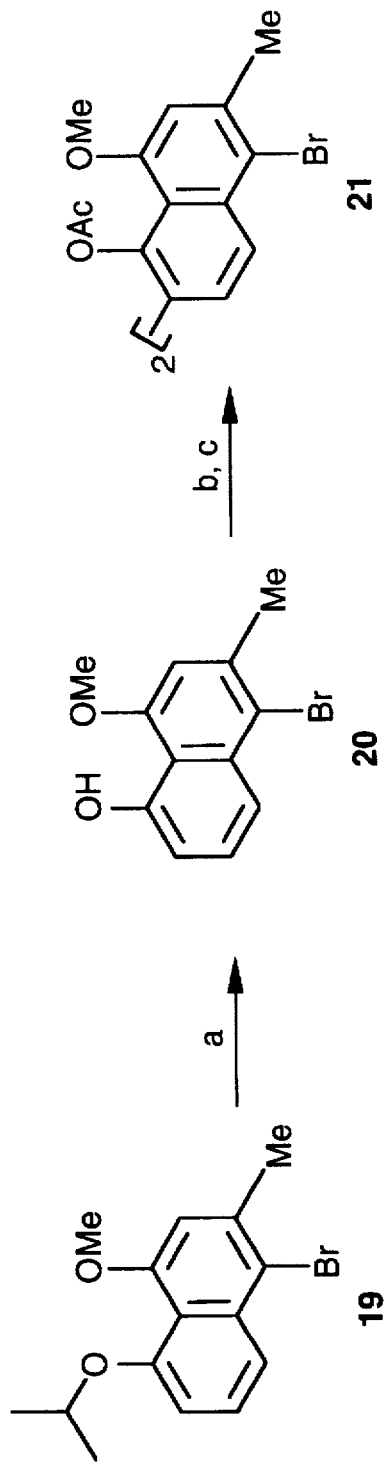

Different modifications can alternatively be selected or incorporated as desired into the aryl halves, either before or after the coupling, to form the biaryl building block Novel binaphthalenes, suitably protected and activated, can also be prepared from other approaches, as further illustrated in FIG. 5. Typical reaction conditions are shown in the corresponding figure legends 5A and 5B. Further details of key reactions typically are as follows.

In a typical example 14 (Bringmann et al. (1994b), supra) is converted to the naphthol 15 with BCl$_3$. After introduction of the SEM-group for the directed ortho metalation, the resulting naphthalene 16 is coupled reductively (compare Lipshultz et al., Tetrahedron Lett., 31, 5567–5570 (1994)) to give 17. A directed metalation-halogenation-sequence with t-BuLi and C$_2$Br$_2$Cl$_4$ (compare Snieckus, Chem. Rev., 90, 879–933 (1990)) yields the functionalized target binaphthalene 18. In another typical example, the known naphthalene 19 is de-isopropylated with BCl$_3$ to give the naphthol 20. After phenolic dimerization with Cu(OAc)$_2$ and NH$_3$ (Rutledge et al., U.S. Pat. No. 4,096,190) and subsequent acetylation with AcCl, the desired binaphthalene 21 is obtained.

Figure 2:
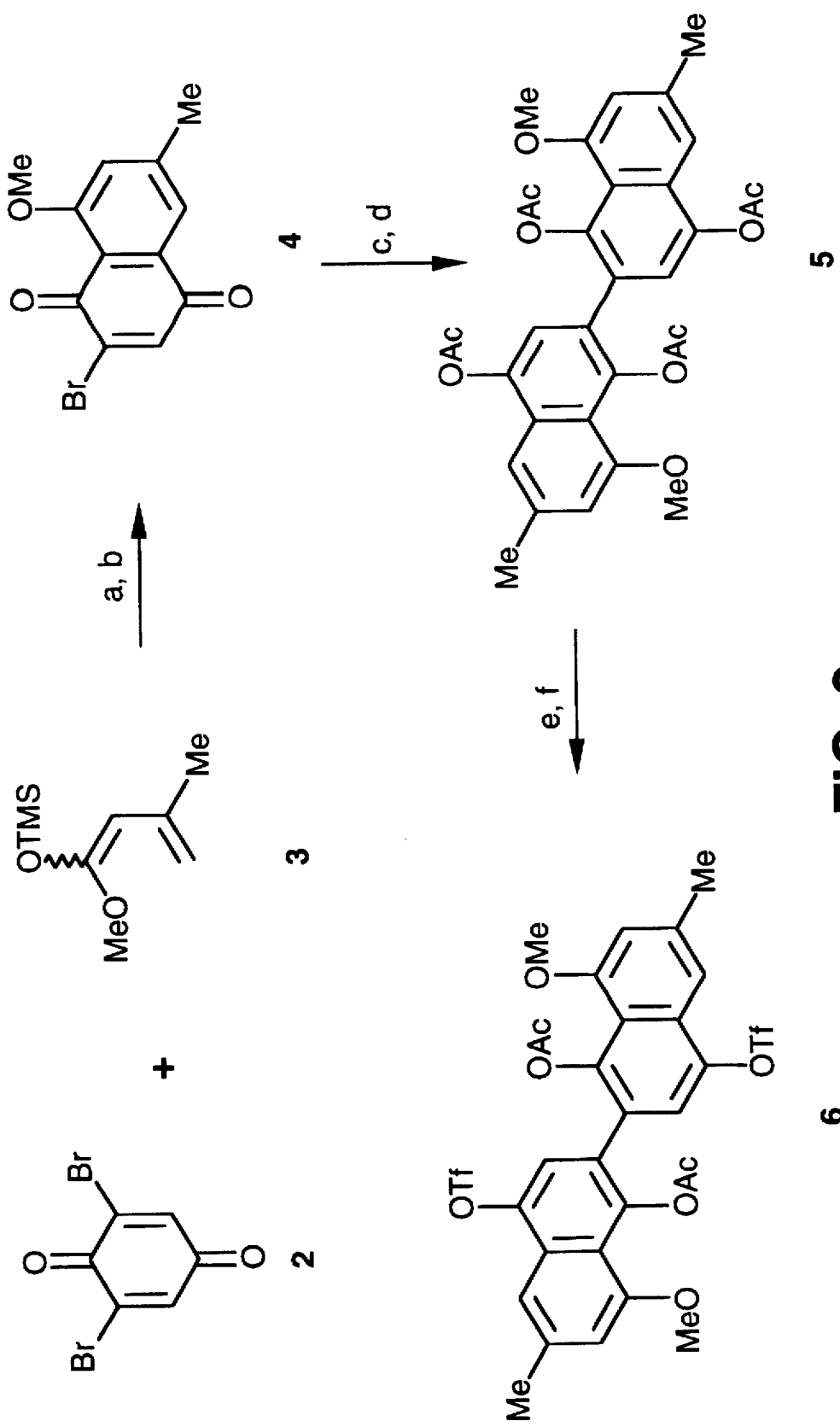
FIG. 2 illustrates the preparation of the suitably protected and activated biaryl building block (6) for synthesis of michellamines A and B. Reaction conditions: a) 0° C., THF, 2 h; stand on silica gel at rt 24 h, 70%; b) MeI, $Ag_2O$, reflux 1 h, 97%; c) DMF, copper bronze, $Pd(PPh_3)_4$, 1.5 h, 130° C. (convert crude directly to 5); d) Zn, $AC_2O$, NaOAc, DMAP, $CH_2Cl_2$, rt, 10 h, 43% overall from 4; d) $CH_2Cl_2$/MeOH, DBU, rt 15 min, 70%; f) $CH_2Cl_2$, 2,6-lutidine, $Tf_2O$, rt, 30 min, 79%.
Figure 6A:
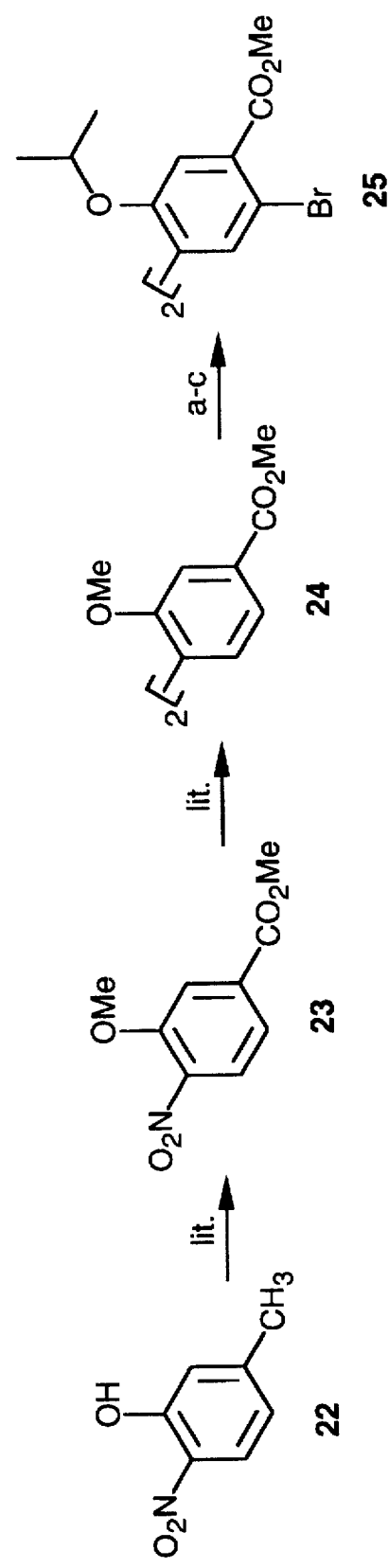
FIGS. 6A–B illustrate various routes of preparation of biphenyl and phenylnaphthalene building blocks For FIG. 6A, typical reaction conditions are: a) $BBr_3$, $CH_2Cl_2$, 0° C.; b) i-$C_3H_7Br$, $K_2CO_3$, acetone, reflux; c) $Br_2$, HOAc, NaOAc, rt. For FIG. 6B, typical reaction conditions are: a) $Br_2$, tert-$BuNH_2$, toluene; b) n-BuLi, -78° C., THF; c) $B(OMe)_3$, THF, aqueous workup; d) $Pd(PPh_3)_4$, $Ba(OH)_2$, $DME/H_2O$; c) $Br_2$, $Ch_2Cl_2$.
Figure 6B:
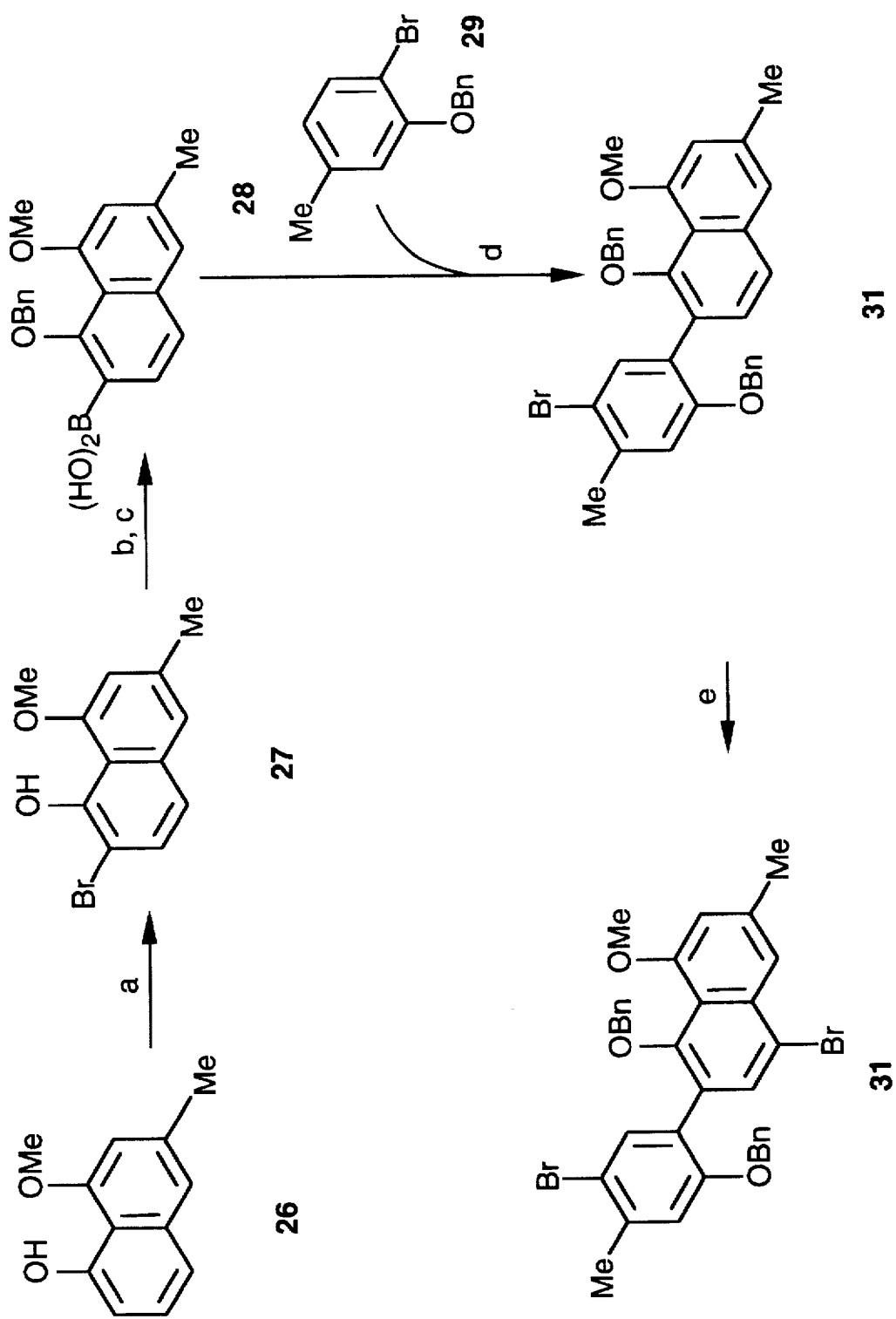

By such approaches as exemplified above and as in FIGS. 2, 4, and 5, suitably protected and activated biaryl building blocks can be obtained as necessary to make any dimeric naphthylisoquinoline compound of prior inventions (Boyd et al., U.S. Pat. No. 5,455,251; and Bringmann et al, U.S. patent application Ser. No. 06/279,339). Furthermore, these same procedures can be used to make other suitably protected and activated biaryl building blocks, which can be used in the method of the present invention to make unprecedented, new dimeric biarylisoquinoline compounds. For example, diverse biphenyl building blocks can be prepared according to the schemes shown in FIG. 6. Such biphenyl building blocks can be used for the synthesis of novel new compounds of the present invention. "Nonsymmetrical" biaryl building blocks, such as phenylnaphthalene building blocks, can also be constructed and used likewise in the method of the present invention to make novel dimeric arylisoquinoline compounds. Typical reaction conditions are shown in the corresponding figure legends 6A and 6B. Further details of key reactions typically are as follows.

In a typical example, the synthesis of 25 starts with the available compound 22, which is converted via 23 to 24 according to literature procedures (Ismail et al., J. Org. Chem., 45, 2243–2246 (1980); Sargent et al., Aust. J. Chem., 41, 1087–1097 (1988)). Cleavage of the methyl ether 24 with BBr3 in CH$_2$Cl$_2$, isopropylation with isopropyl bromide in acetone and K$_2$CO$_3$, and subsequent bromination with bromine in HOAc/NaOAc affords the biphenyl building block 25.

In another typical example, the synthesis starts with the selective bromination of the phenol 26 with bromine and tert-BuNH$_2$ in toluene (analogue to Pearson et al., J. Org. Chem., 32, 2358–2360 (1967)) to give 27. The boronic acid 28 is obtained after lithiation of 27 with n-BuLi and subsequent treatment with B(OMe)$_3$ and aqueous workup. The coupling with the bromo-compound 29, which may be obtained by bromination of m-cresol and subsequent benzylation, under the same coupling conditions as in the case of Example 1 (FIG. 3), yields the nonsymmetrical biaryl 30, which is converted to the dibromo compound 31.

Example 3:

Preparation of Various

Isoquinoline Building Blocks

Figure 7A:
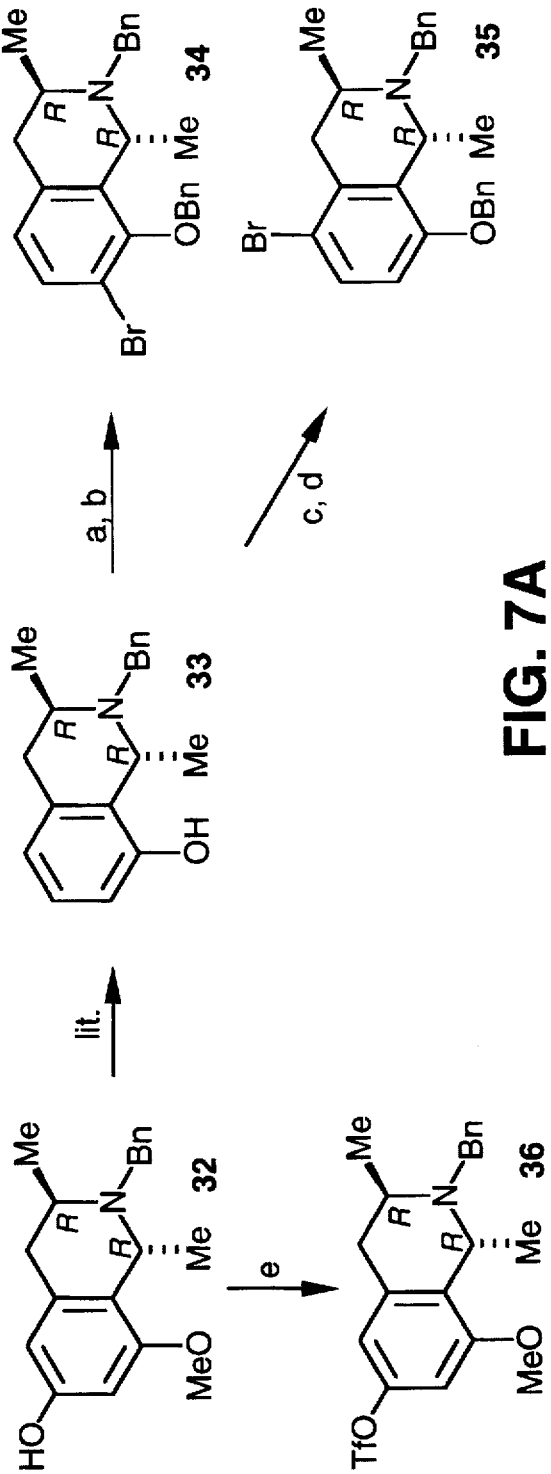
FIGS. 7A–B illustrate various routes of preparation of different isoquinoline building blocks.
Figure 7B:
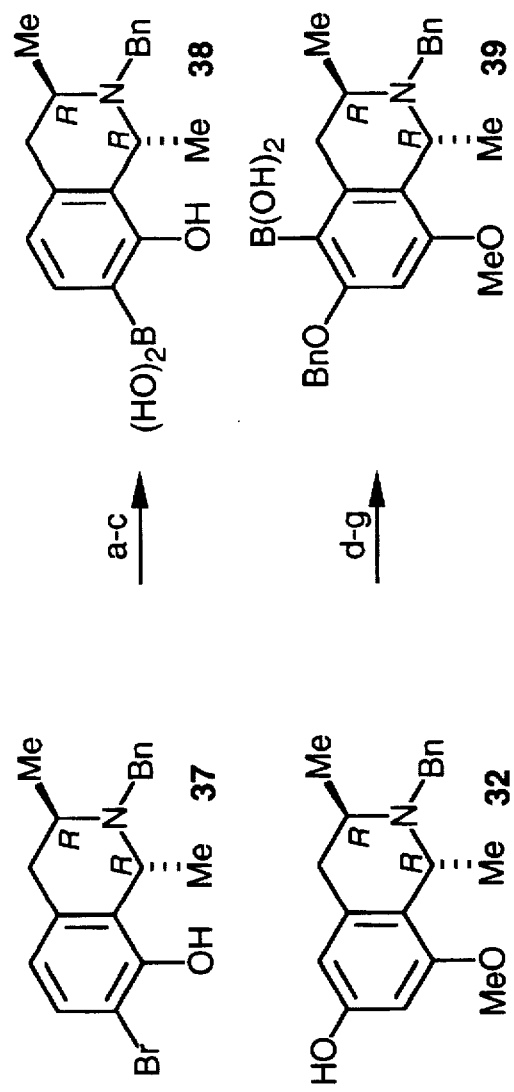

This example further illustrates some selected different variations in the isoquinoline building blocks which may be obtained or prepared and used in the method of the present invention. For instance, diverse electrophilic and nucleophilic isoquinoline building blocks may be made according to the schemes summarized in FIGS. 7A and 7B, respectively. Typical reaction conditions are shown in the corresponding figure legends. Further details of key reactions typically are as follows.

In typical examples for electrophilic isoquinoline building blocks, 32 HBr is converted to 33 according to literature procedures (Bringmann et al., *Liebigs Ann. Chem.*, 877–888 (1993)). 33 and tert-BuNH$_2$ are then dissolved in dry toluene and bromine is added. After workup and subsequent treatment with BnBr and K$_2$CO$_3$ in acetone, 34 is obtained. For the benzylation of 33, BnBr and K$_2$CO$_3$ are added to a solution of 33 in acetone. The bromination yields the compound 35. Reaction conditions for the synthesis of 36 are typical (compare Chapman et al., *Synthesis*, 591–592 (1971)). For preparation of 36, 32 is dissolved in dry CH$_2$Cl$_2$ and TlOEt is added under argon; subsequent treatment with Tf$_2$O and following workup affords the desired isoquinoline derivative.

In typical examples for nucleophilic isoquinoline building blocks, 37, which can be obtained by selective bromination of 33 (for the synthesis of 33 see Bringmann et al. (1993), supra), is benzylated with BnBr. Subsequent treatment with n-BuLi yields the lithiated isoquinoline, to which B(OMe)$_3$ is added. Aqueous workup affords the boronic acid 38. For synthesis of the isoquinoline boronic acid 39, after benzylation of 32 (for the synthesis of 32 see Bringmann et al. (1993), supra) with BnBr and selective bromination, the resulting bromoisoquinoline is treated with n-BuLi and subsequently with B(OMe)$_3$; aqueous workup afforded the desired boronic acid derivative.

Example 4:

Construction of a Nonsymmetrical Dimeric

Arylisoquinoline Alkaloid by Sequential Rather Than

Figure 8:
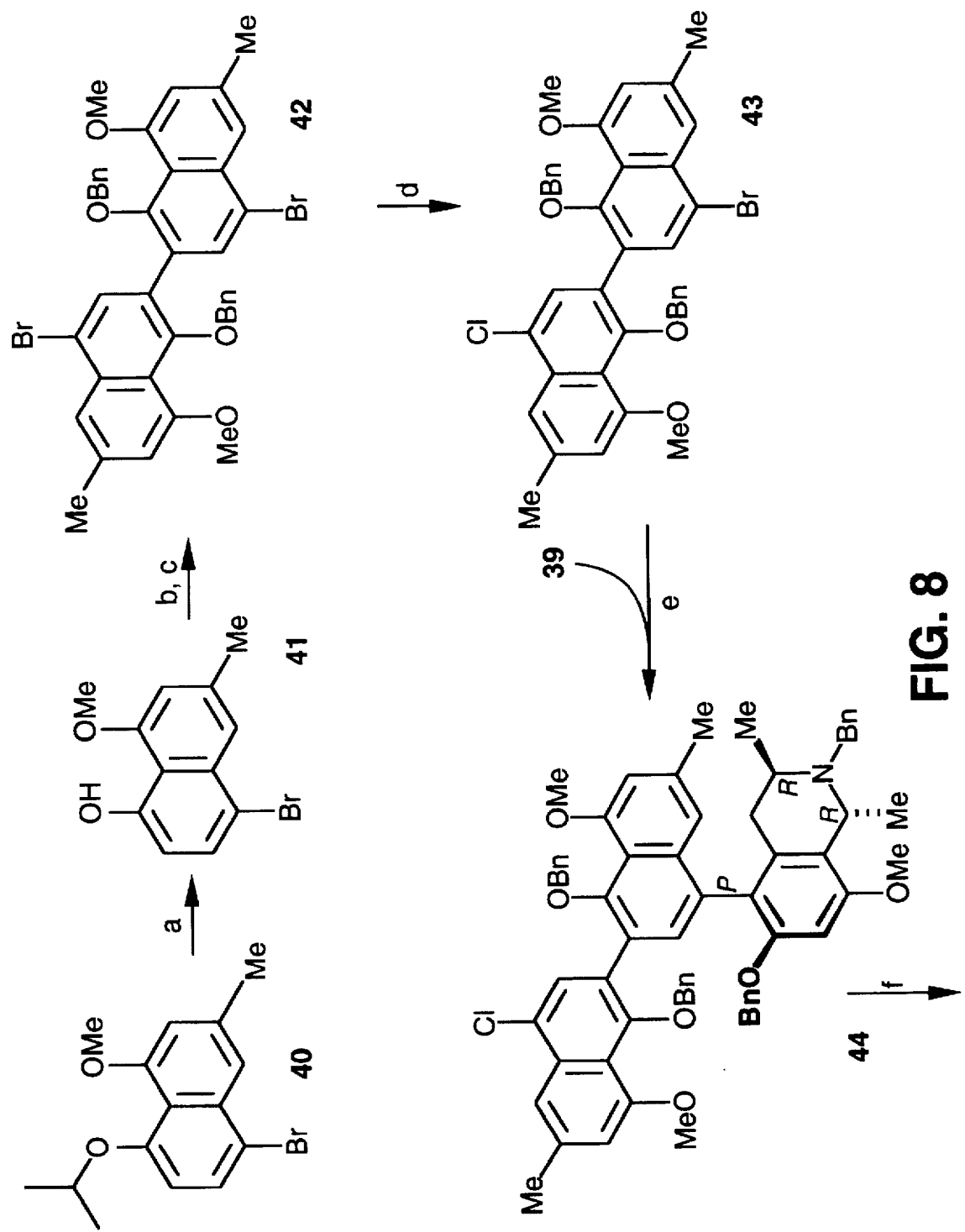
FIG. 8 illustrates preparation of a nonsymmetrical dimeric arylisoquinoline alkaloid by sequential coupling of different first and second isoquinoline building blocks to a biaryl building block. Typical reaction conditions are: a) $BCl_3$, $CH_2Cl_2$; b) $Cu(OAc)_2$, $NH_3$, 2,6-xylenol; c) BnBr, $K_2CO_3$, acetone; d) n-BuLi (1 eq), NCS, $Et_2O$; e) $Pd(PPh_3)_4$, $Ba(OH)_2$, $DME/H_2O$; f) n-BuLi, $C_2Br_2Cl_4$, THF; g) $Pd(PPh_3)_4$, $Ba(OH)_2$, $DME/H_2O$; h) $H_2$, Pd/C(10%), EtOH.
Figure 8:
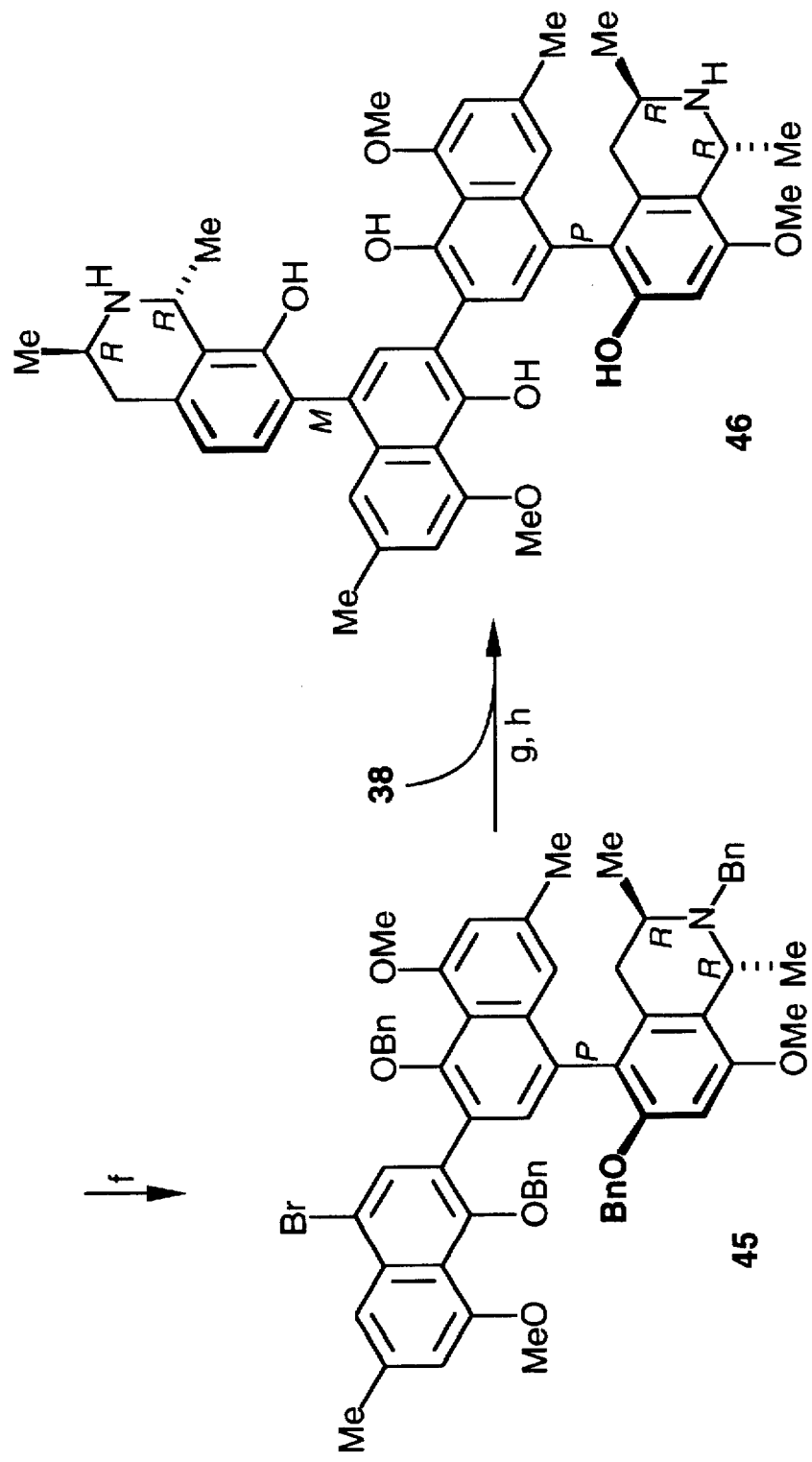
Figure 9A:
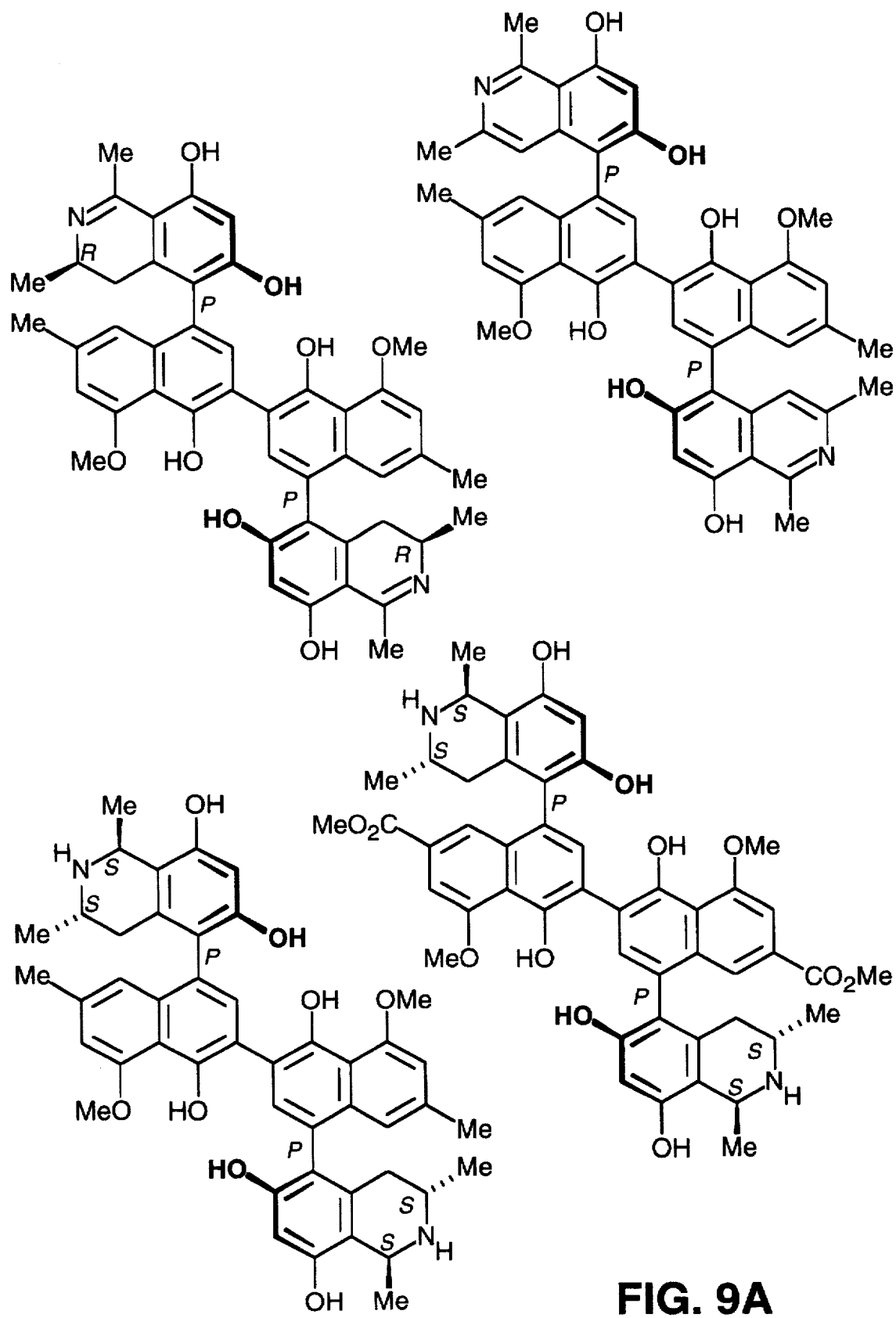
FIGS. 9A–G illustrate other specific examples of dimeric arylisoquinoline alkaloids which can be prepared according to the method of the present invention.
Figure 9B:
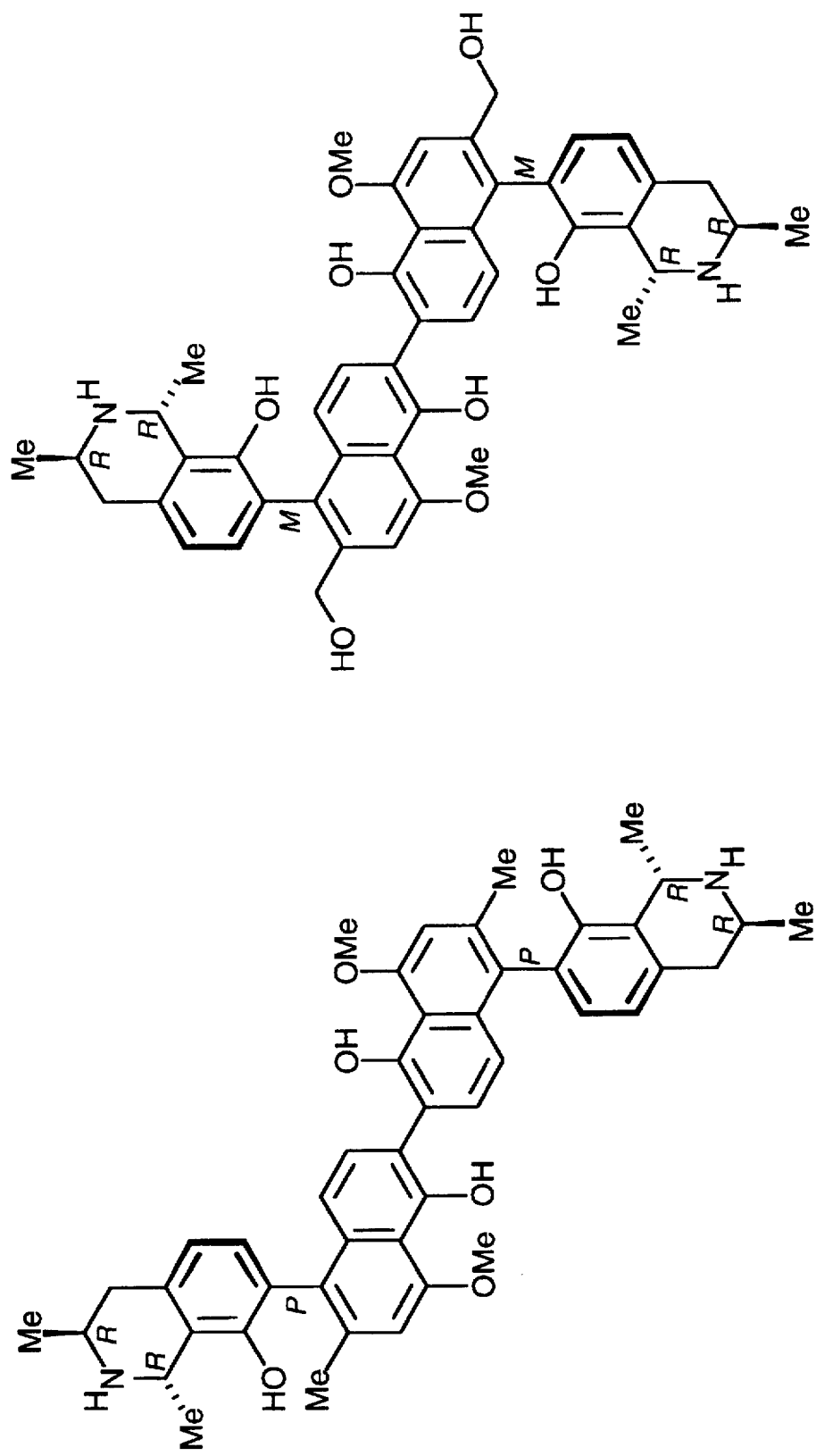
Figure 9B:
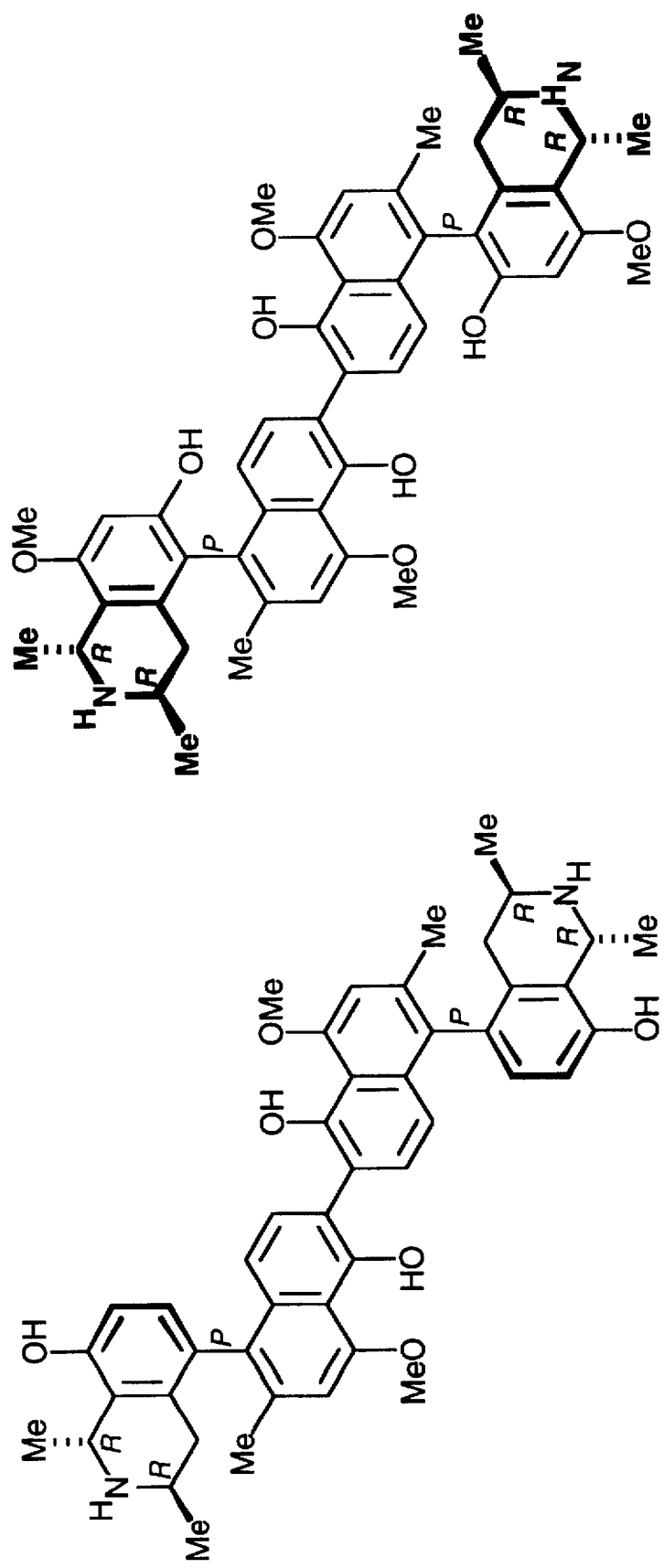
Figure 9C:
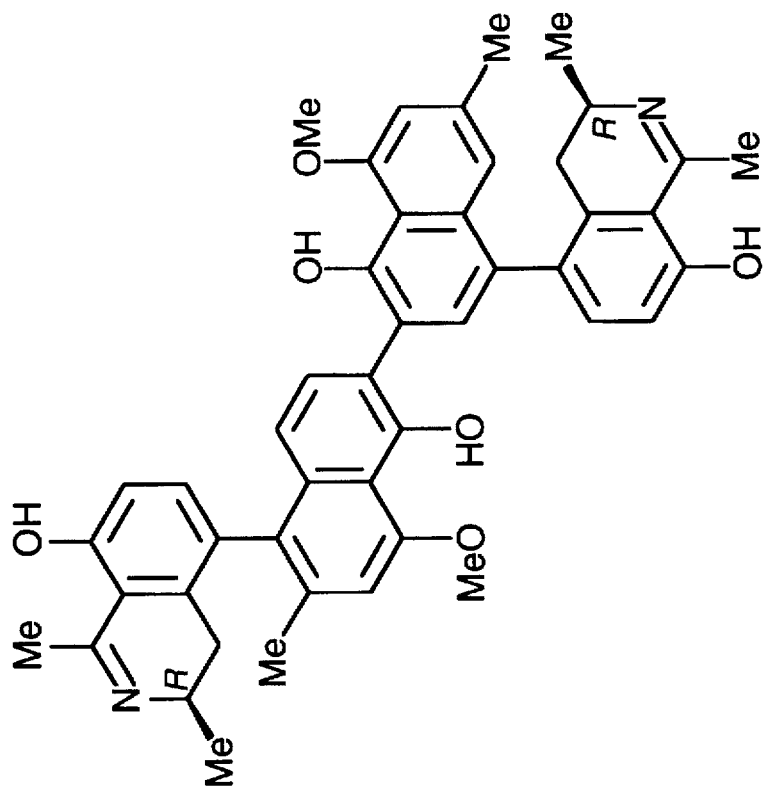
Figure 9C:
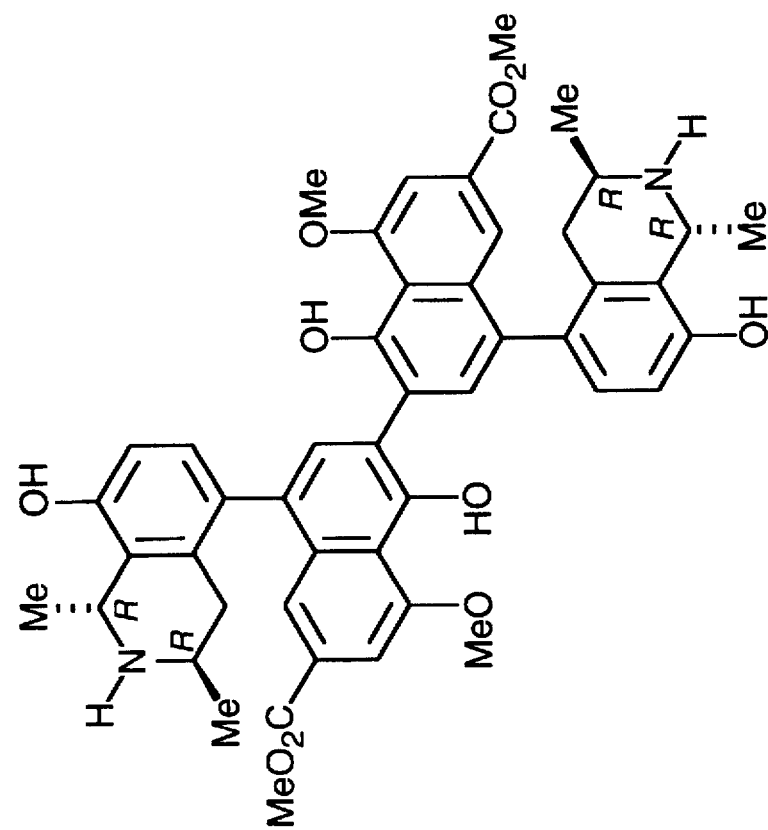
Figure 9C:
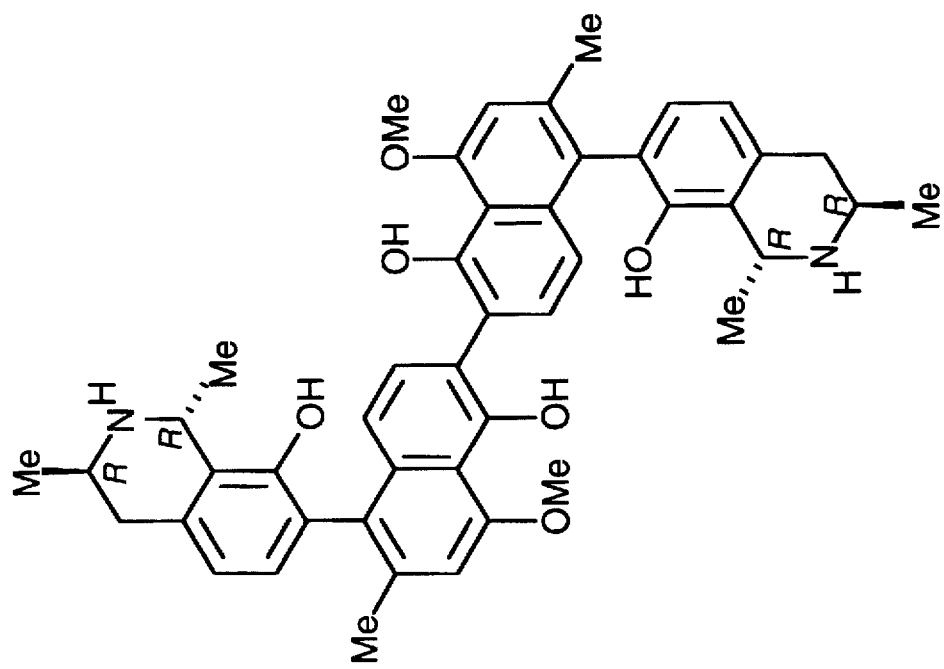
Figure 9C:
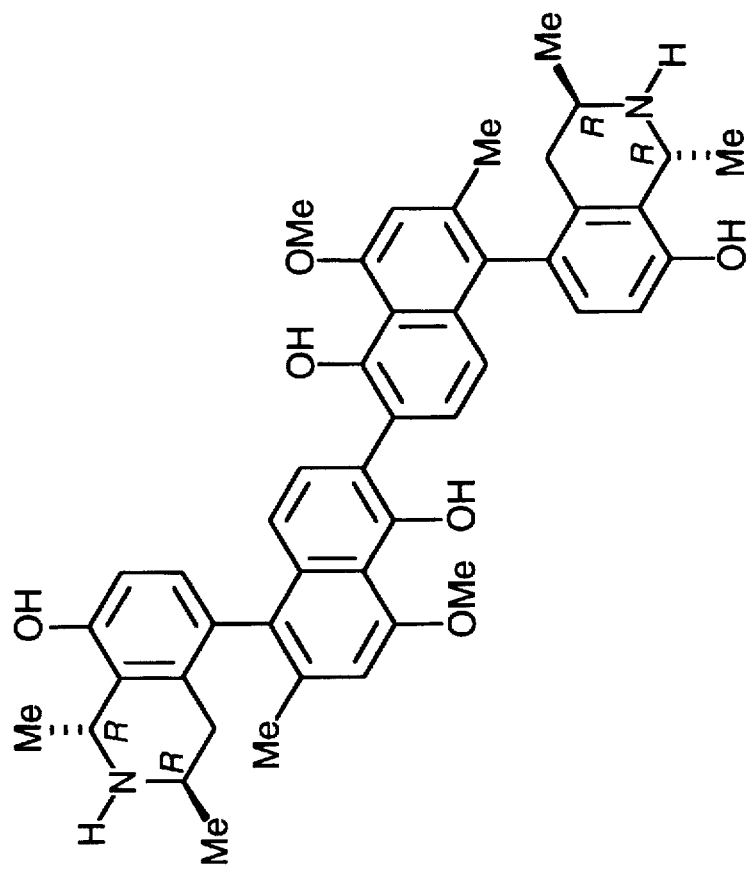
Figure 9D:
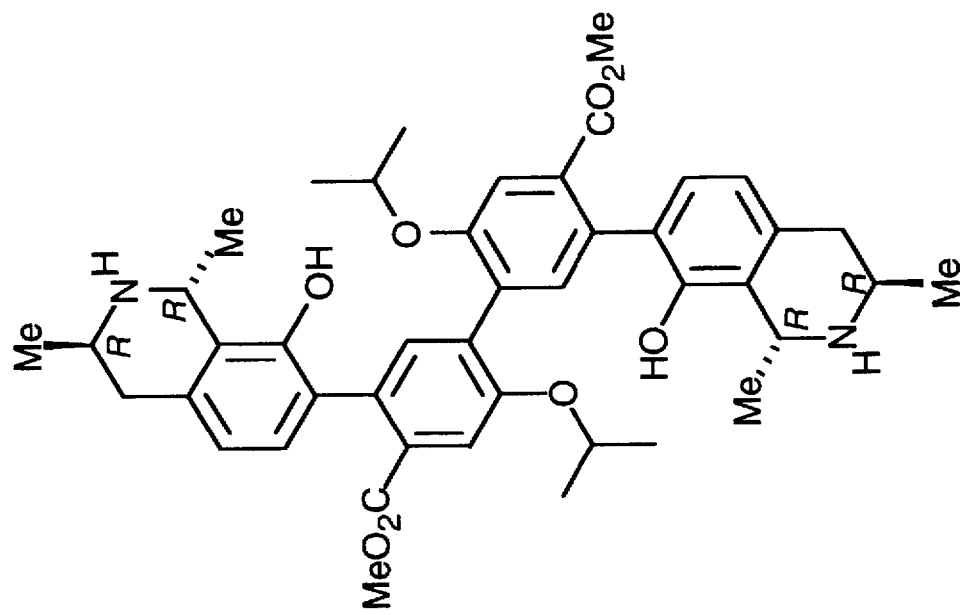
Figure 9D:
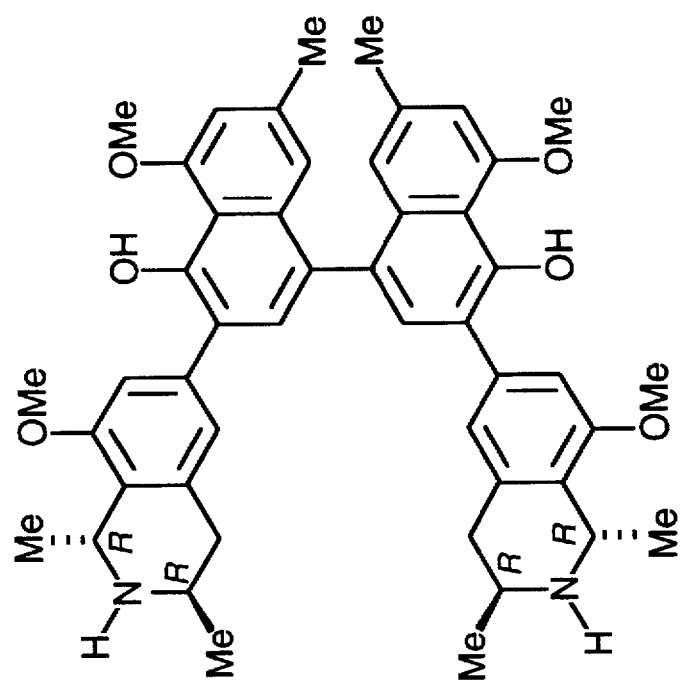
Figure 9E:
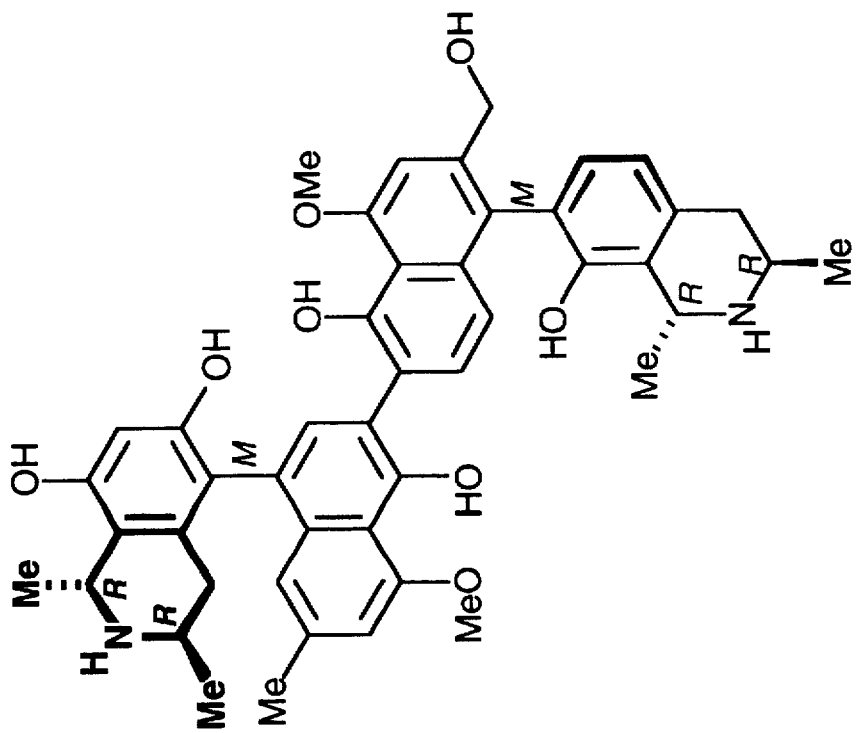
Figure 9E:
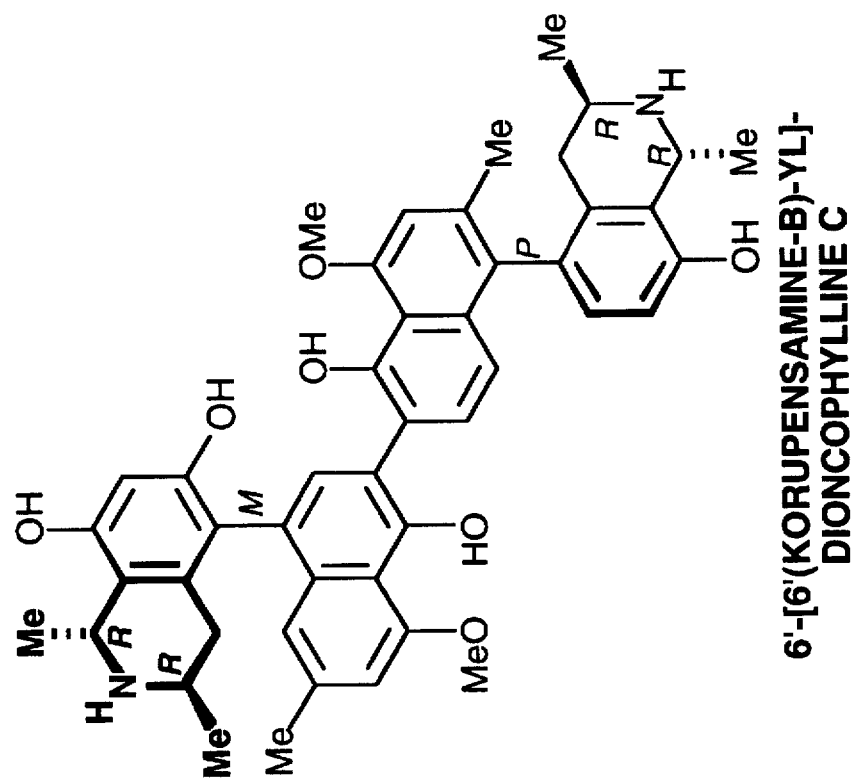
Figure 9F:
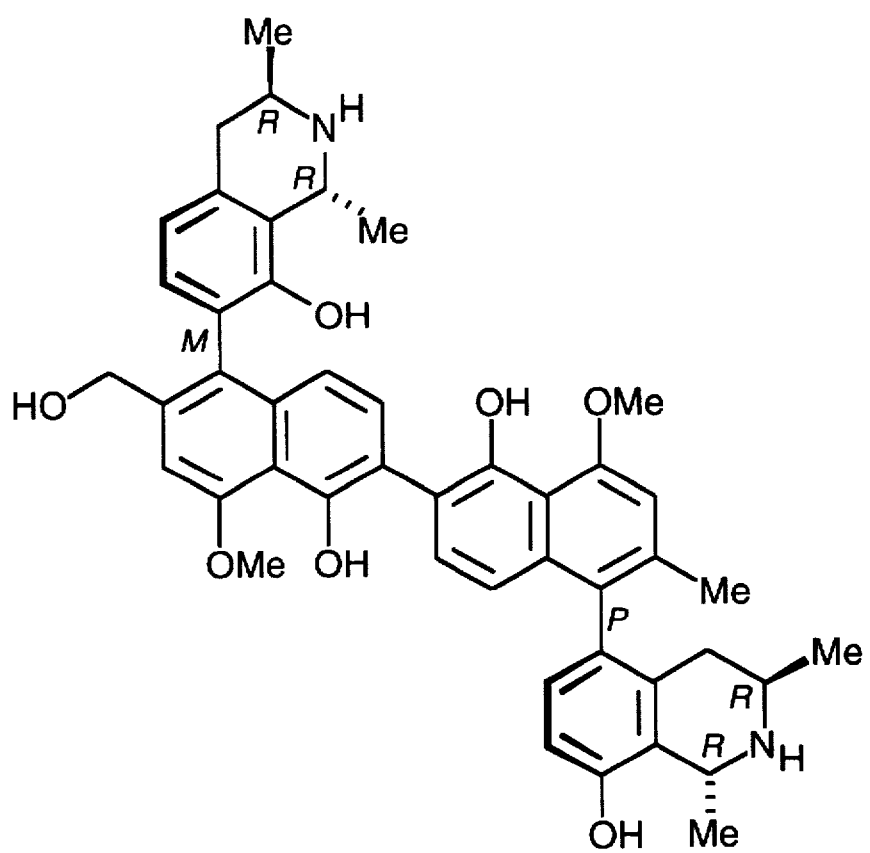
Figure 9G:
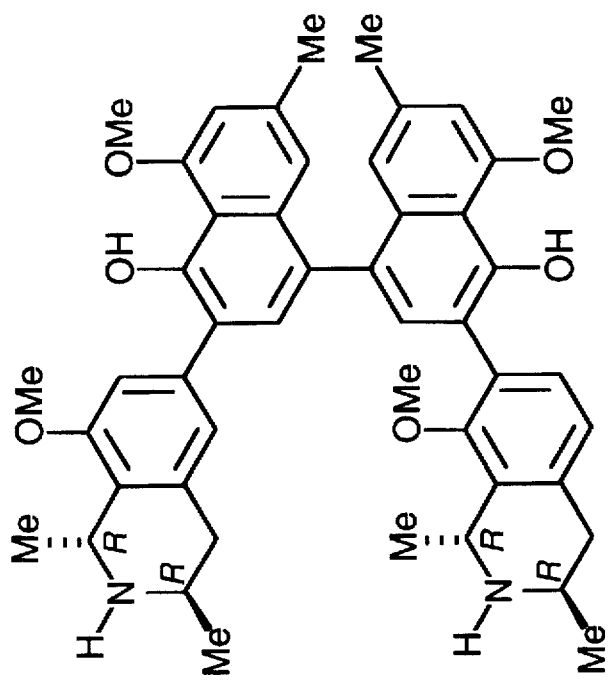
Figure 9G:
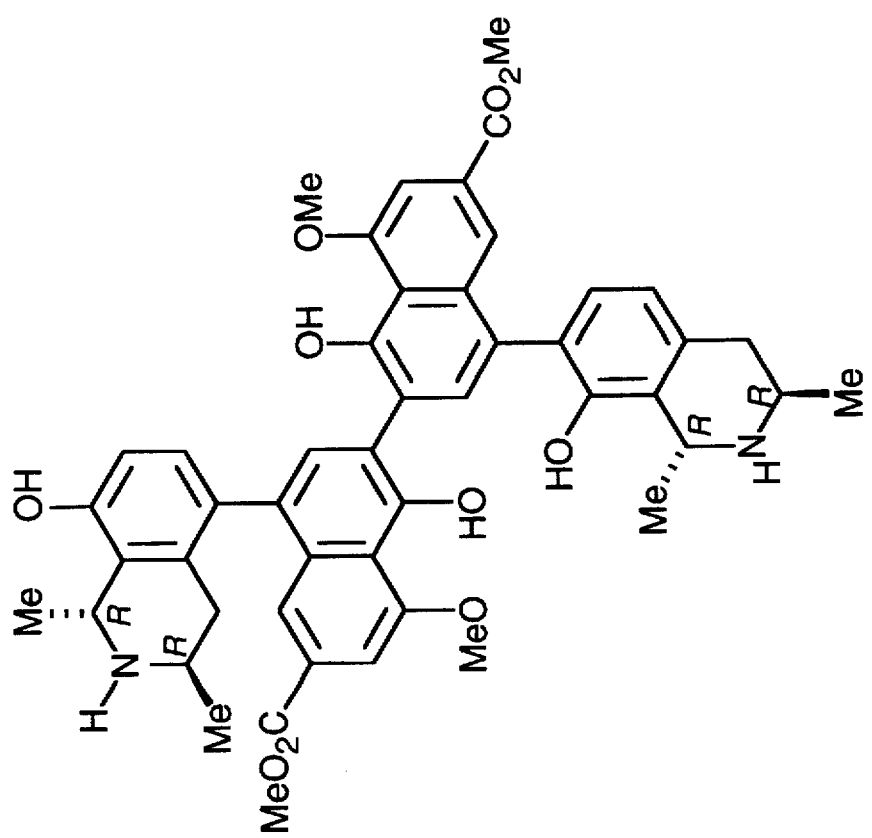
Figure 9G:
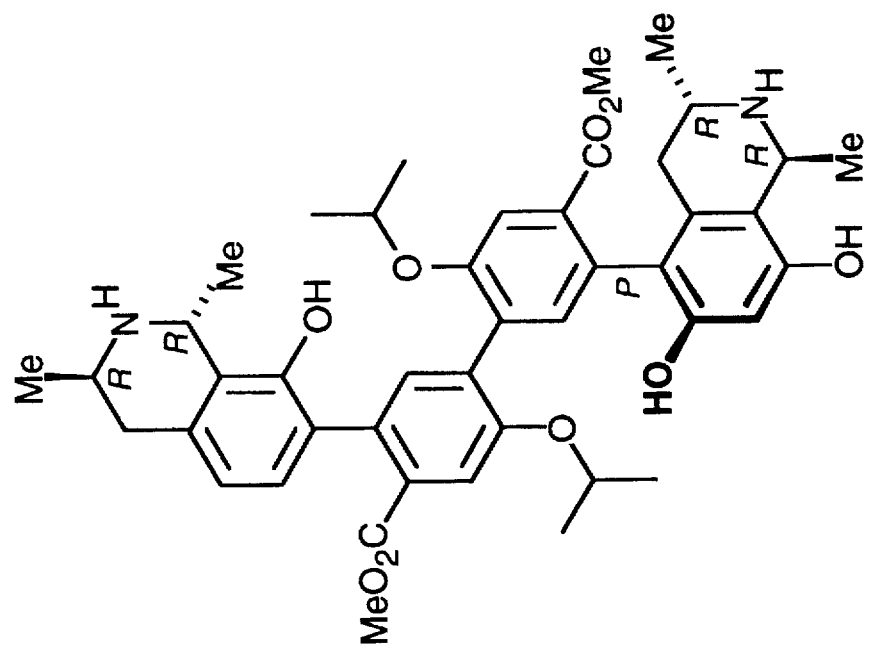
Figure 9G:
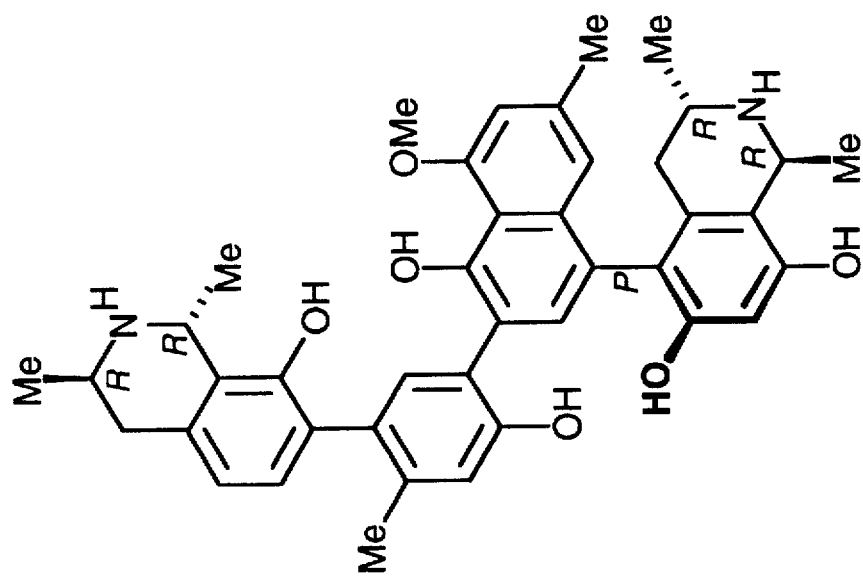

Simultaneous Coupling of the Isoquinoline Building Blocks to the Biaryl Building Block Whereas Example 1 illustrates the preparation of a dimeric arylisoquinoline alkaloid by simultaneous coupling of two identical isoquinoline building blocks with a biaryl building block, this example illustrates the sequential coupling of a first and then a second isoquinoline building block to a biaryl building block. This may be preferred when the first and second isoquinoline building blocks are not identical. A typical reaction sequence is summarized in FIG. 8. Typical reaction conditions are shown in the corresponding figure legend Further details of key reactions typically are as follows.

The known naphthalene 40 (Bringmann et al. (1994b), supra) is deisopropylated with BCl$_3$ to give the naphthol 41, which is then oxidatively coupled with Cu(oAc)$_2$ and NH$_3$ (compare Rutledge et al., U.S. Pat. No. 4,096,190). Protection of the free hydroxy functions with BnBr and K$_2$CO$_3$ in acetone yields the binaphthalene 42, which is converted, after mono-lithiation with n-BuLi and subsequent treatment with N-chloro-sucinimide, to the bromo-chlorobinaphthalene 43. Compound 43 is selectively coupled under usual coupling conditions (see Example 1) with the isoquinoline-boronic acid 39 to give the teraryl 44, which is converted after lithiation and subsequent treatment with C$_2$Br$_2$Cl$_4$ to the bromo-compound 45. The coupling with the boronic-acid 38 affords the corresponding quateraryl, which yields, after deprotection of the benzyl groups with H$_2$ at Pd/C (10%) the nonsymmetrical dimer 46.

Example 5:

Diversity of Homodimeric and Heterodimeric

Arylisoquinoline Alkaloids of the Present Invention

The present invention allows an exceedingly broad range of variations to be incorporated individually in the first and second isoquinoline building blocks and in the biaryl building bock, before and/or after coupling to form the homodimeric or heterodimeric arylisoquinoline alkaloid. Consequently, a compound of the present invention may be drawn from an extraordinary diversity of variations around the dimeric arylisoquinoline alkaloid theme. FIGS. 9A–G provide additional specific illustrations of such homodimers, heterodimers having different isoquinoline parts but a symmetrical central biaryl core, and heterodimers having either the same or different isoquinoline parts and a nonsymmetrical central biaryl core.

All of the references cited herein, including patents, patent applications, literature publications, and the like, are hereby incorporated in their entireties by reference.

While this invention has been described with an emphasis upon preferred embodiments, it will be obvious to those of ordinary skill in the art that variations of the preferred compounds and methods may be used and that it is intended that the invention may be practiced otherwise than as specifically described herein- Accordingly, this invention includes all modifications encompassed within the spirit and scope of the invention as defined by the following claims

What is claimed is:

1. A method of preparing a dimeric arylisoquinoline alkaloid comprising the steps of:

(a) obtaining first and second isoquinoline building blocks, which are either the same or different, each having protective group(s) at desired site(s), each containing an activation group at a desired coupling site, and each being a tetrahydroisoquinoline, dihydroisoquinoline, or fully aromatic isoquinoline building block, (b) obtaining a biaryl building block having protective group(s) at desired site(s), a first activation group at a first desired coupling site, and a second activation group at a second desired coupling site, (c) coupling said first isoquinoline building block at said desired first coupling site, (d) coupling said second isoquinoline building block at said second coupling site of said biaryl building block, and (e) optionally deprotecting desired site(s) on said biaryl building block.

2. The method of claim 1, wherein said first and second isoquinoline building blocks are simultaneously coupled to said biaryl building block.

3. The method of claim 1, wherein said second activation group is introduced at said second desired coupling site in said biaryl building block after said first isoquinoline building block is coupled to said biaryl building block, and said second isoquinoline building block is coupled to said biaryl building block after said first isoquinoline building block is coupled to said biaryl building block.

4. The method of claim 3, wherein said desired site(s) on said biaryl building block are deprotected prior to introducing said second activation group at said second desired coupling site in said biaryl building block.

5. The method of claim 1, which method further comprises:

(f) removing said protective groups from the dimeric arylisoquinoline alkaloid, and (g) purifying the dimeric arylisoquinoline alkaloid.

6. The method of claim 5, wherein said purifying comprises purifying by HPLC.

7. The method of claim 1, wherein one or more of said protective groups is selected from the group consisting of benzyl, acetyl, and formyl.

8. The method of claim 1, wherein said activation groups for said isoquinoline building blocks may be the same or different and each is selected from the group consisting of boronic acid, trialkylstannyl, halogen, and O-triflate groups.

9. The method of claim 8, wherein said activation groups for said isoquinoline building blocks may be the same or different and each is selected from the group consisting of boronic acid and trialkylstannyl groups.

10. The method of claim 1, wherein said first and second activation groups for said biaryl building block are the same or different and each is selected from the group consisting of boronic acid, trialkylstannyl, halogen, and O-triflate groups.

11. The method of claim 10, wherein said first and second activation groups for said biaryl building block are the same or different and each is selected from the group consisting of halogen and O-triflate groups.

12. The method of claim 1, wherein said coupling is effected by transition metal catalysis.

13. The method of claim 12, wherein said coupling is effected using Pd.

14. The method of claim 1, wherein said activation group for said first and second isoquinoline building blocks is a boronic acid group and said first and second activation groups for said biaryl building block are both O-triflate.

15. The method of claim 1, wherein said isoquinoline building blocks are the same and each is a tetrahydroisoquinoline having methyl groups at C-1 and C-3.

16. The method of claim 15, wherein said biaryl building block is a binaphthalene.

17. The method of claim 1, wherein said biaryl building block is biphenyl.

18. The method of claim 1, wherein said biaryl building block is phenylnaphthalene.

* * * * *